(12) United States Patent
Franck et al.

(10) Patent No.: US 8,669,378 B2
(45) Date of Patent: Mar. 11, 2014

(54) PROCESS FOR SYNTHESIZING EPICCONONE ANALOGS

(75) Inventors: Xavier Franck, Bois Guillaume (FR); Philippe Peixoto, Rouen (FR); Peter Helmuth Karuso, Killara (AU)

(73) Assignees: Universite de Rouen, Mont-Saint-Aignan (FR); Centre National de la Recherche Scientifique-CNRS, Paris (FR); Institut National des Sciences Appliquees de Rouen, Saint-Etienne du Rouvray (FR); Macquarie University, Sidney (AU)

( * ) Notice: Subject to any disclaimer, the term of this patent is extended or adjusted under 35 U.S.C. 154(b) by 0 days.

(21) Appl. No.: 13/503,880

(22) PCT Filed: Oct. 25, 2010

(86) PCT No.: PCT/EP2010/066064
§ 371 (c)(1),
(2), (4) Date: Apr. 25, 2012

(87) PCT Pub. No.: WO2011/051225
PCT Pub. Date: May 5, 2011

(65) Prior Publication Data
US 2012/0214194 A1    Aug. 23, 2012

(30) Foreign Application Priority Data
Oct. 26, 2009  (FR) ..................... 09 57495

(51) Int. Cl.
*C07D 307/00* (2006.01)
(52) U.S. Cl.
USPC ....................................... 549/299

(58) Field of Classification Search
USPC .......................................................... 549/299
See application file for complete search history.

(56) References Cited

U.S. PATENT DOCUMENTS

2008/0085993 A1*  4/2008  Bell et al. ................... 530/300

FOREIGN PATENT DOCUMENTS

WO    WO 01/81351    11/2001

OTHER PUBLICATIONS

Dorwald F. A. Side Reactions in Organic Synthesis, 2005, Wiley: VCH, Weinheim p. IX of Preface p. 1-15.*
International Search Report dated Jun. 19, 2001 for Application No. PCT/AU2001/00472.

* cited by examiner

*Primary Examiner* — Nizal Chandrakumar
(74) *Attorney, Agent, or Firm* — Frost Brown Todd LLC

(57) ABSTRACT

The present invention relates to a process for the total synthesis of epicconone analogs of formula (I):

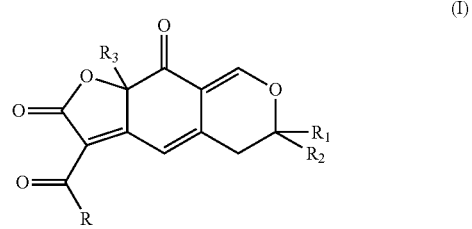

The invention also relates to novel epicconone analogs.

2 Claims, 1 Drawing Sheet

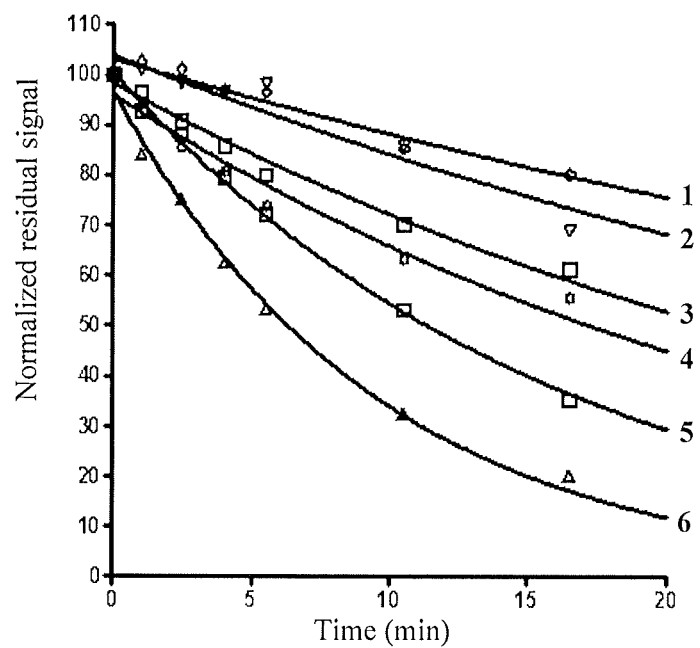

PROCESS FOR SYNTHESIZING EPICCONONE ANALOGS

TECHNICAL FIELD OF THE INVENTION

The present invention relates to a process for synthesizing epicocconone analogs.

PRIOR ART

Epicocconone, or 5,6-dihydro-3-[(1Z,4E,6E,8E)-1-hydroxy-3-oxo-1,4,6,8-decatetraenyl]-6-hydroxymethyl-9a-methyl-2H-furo[3,2g][2]benzopyran-2,9-(9aH)-dione, is a chemical compound that was isolated from the fungus *Epicoccum nigrum* and chemically resolved in 2003 by P. J. Bell and P. Karuso ("Epicocconone, a novel fluorescent compound from the fungus *epicoccum nigrum*" *J. Am. Chem. Soc.* (2003), 125(31), 9304-5). The chemical formula of epicocconone is as follows:

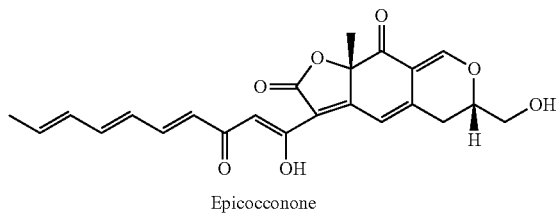 [SMILES: C/C=C/C=C/C=C/C(=O)/C=C(\O)C1=C2C=C3C[C@@H](CO)OC=C3C(=O)[C@@]2(C)OC1=O]

Epicocconone

This natural product was found to have noteworthy properties: its novel chemical structure allows it to bond covalently to amine functions, forming an enamine adduct that fluorescences in the red range, more specifically at about 600 nm, when it is subjected to UV-Vis radiation, for example at 395 nm or 520 nm. This molecule thus has a very large Stokes shift (difference between the absorption wavelength and the emission wavelength), of about 100 nm.

In addition, this molecule has other advantageous characteristics, such as a small size (410 amu (atomic mass units)) and good solubility both in water and in lipid bilayers.

It is, inter alia, for these reasons that epicocconone is of great interest in the field of life sciences. Specifically, fluorescent compounds are used for detecting and visualizing biological compounds or phenomena. They are thus very useful for diagnostic purposes, for demonstrating the activity of an enzyme, for visualizing proteins both in biological matrices, for example in vivo, and in other media, for example in aqueous solution, in electrophoresis gels. They may also be attached to solid supports or monoclonal antibodies.

In this context, epicocconone has the advantage of bonding to the amine functions of proteins. The adduct formed may be readily excited at specific wavelengths of 488 nm or 520 nm, chosen especially to avoid the autofluorescence of proteins and which are the lengths of the commonest laser sources. It responds by emitting light at a longer wavelength and with a large Stokes' shift, which makes it possible to overcome the problem of overlap between the absorbed and emitted wavelengths.

This molecule and some of its analogs have been described in international patent application WO 01/81351. Some of its applications have already been described in said patent application. Other applications are described in international patent applications WO 2004/085 546 and WO 2007/051 256. Epicocconone is currently marketed under the name LavaPurple (formally Deep Purple Total Protein Stain or Fluoroprofile) by the company GelCompany or FluoroTechnics for applications in proteomics and more generally in biology.

The epicocconone currently available on the market is isolated from a species of fungus. This biological production route is described, for example, in the above-cited patent applications. To overcome the problems of supply, yield and reproducibility associated with the biological processes, it would be desirable to be able to obtain epicocconone via chemical synthesis. It would also be desirable also to have access to molecules that are similar to it, as regards their structure and their properties, in order to broaden the spectrum of available molecules. However, no total synthesis of this molecule and its analogs has ever been presented.

SUMMARY OF THE INVENTION

The present invention relates to a process for synthesizing compounds of formula (I)

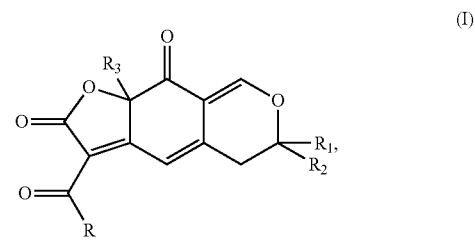

tautomers thereof, stereoisomers thereof and mixtures thereof, in which

R1, R2 and R3 are each independently a hydrogen, a halogen,
- a C1 to C20 alkyl chain, which may optionally comprise one or more heteroatoms chosen from O, N, S and P, which may be optionally substituted with one or more identical or different substituents chosen from a halogen and a hydroxyl, oxo, amino, amido, ether, ester or urea group,
- a C2 to C20 alkenyl chain, which may optionally comprise one or more heteroatoms chosen from O, N, S and P, which may be optionally substituted with one or more identical or different substituents chosen from a halogen and a hydroxyl, oxo, amino, amido, ether, ester or urea group, R is a hydrogen, a halogen,
or R represents -A-C, A denoting a chemical bond or a linear or branched divalent radical, containing 1 to 20 carbon atoms, which may optionally comprise one or more heteroatoms chosen from O, N, S and P, and which may comprise one or more unsaturations, and which may optionally be substituted with one or more identical or different substituents chosen from a halogen, a hydroxyl group and an oxo group, and C being a hydrogen or a monocyclic or polycyclic group, which may optionally comprise one or more heteroatoms chosen from O, N, S and P, optionally containing one or more unsaturations and possibly being substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of the poly(alkyloxy) type of formula —O—([C1 to C4 alkyl chain]-O)$_n$—(C1 to C4 alkyl chain), n being 1 to 10, comprising the step of reacting the compound of formula (II)

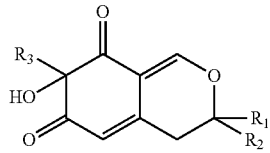

(II)

in which R1, R2 and R3 are as defined previously,
with a compound of formula (III)

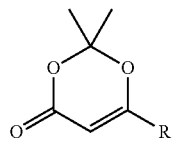

(III)

or a silyl derivative thereof,
in which R is as defined previously,
in the presence of a base.

The present invention also relates to compounds of formula (I')

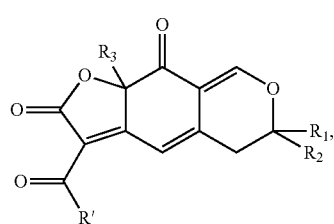

(I')

tautomers thereof, stereoisomers thereof and mixtures thereof, in which
R1, R2 and R3 are each independently a hydrogen, a halogen,
  a C1 to C20 alkyl chain, which may optionally comprise one or more heteroatoms chosen from O, N, S and P, which may be optionally substituted with one or more identical or different substituents chosen from a halogen and a hydroxyl, oxo, amino, amido, ether, ester or urea group,
  a C2 to C20 alkenyl chain, which may optionally comprise one or more heteroatoms chosen from O, N, S and P, which may be optionally substituted with one or more identical or different substituents chosen from a halogen and a hydroxyl, oxo, amino, amido, ether, ester or urea group,
R' represents -A-C',
  A denoting a chemical bond or a linear or branched divalent radical, containing 1 to 20 carbon atoms, which may optionally comprise one or more heteroatoms chosen from O, N, S and P, and which may comprise one or more unsaturations, and which may be optionally substituted with one or more identical or different substituents chosen from a halogen, a hydroxyl group and an oxo group, and C' being a monocyclic or polycyclic group, which may optionally comprise one or more heteroatoms chosen from O, N, S and P, optionally containing one or more unsaturations and being optionally substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl chain]-O)$_n$—(C1 to C4 alkyl chain), n being 1 to 10.

Chemical compounds described in the present patent application contain one or more asymmetric centers and/or 1,3-diketone structures. In general, the compounds of the present invention comprise their stereoisomers (diastereoisomers, enantiomers), in pure form or as a mixture, racemic mixtures thereof, and tautomers thereof.

DETAILED DESCRIPTION OF THE INVENTION

The compounds of formula (I) have the particular feature of having the epicocconone skeleton. The synthesis of these compounds via a novel route based on the introduction of acyl furanones from dioxin-4-ones is described herein.

The present invention thus relates to the process for synthesizing compounds of formula (I) from the compounds of formulae (II) and (III), or a silyl derivative thereof, as defined previously.

According to one embodiment of the present invention, the compound of formula (I) is a compound of formula (I') according to the invention.

According to another embodiment of the present invention, R in the compound of formula (I) represents a hydrogen or a halogen.

According to yet another embodiment of the present invention, R in the compound of formula (I) represents -A-C in which C is a hydrogen.

This reaction consists in introducing a furanone group into the compound of formula (II). Examples of acyl furanone synthesis have been described starting from β-keto ester or from diketenes (V. I. Tyvorskii, A. S. Kukharev, O. G. Kulinkovich, N. De Kimpe and K. A. Tehrani, "A convenient synthesis of 3-functionalized 5-alkoxymethyl- and 5-phenoxymethyl-2(5H)-furanones and their transformations into related epoxy and methylene lactones" *Tetrahedron* (1998), 54(9), 1801-1808; S. Kuwahara, M. Moriguchi, K. Miyagawa, M. Konno and O. Kodama "Synthesis and absolute configuration of syringolide 2, an elicitor from *Pseudomonas syringae* pv. tomato" *Tetrahedron Letters* (1995), 36(18), 3201-3202; J. L. Wood, S. Jeong, A. Salcedo and J. Jenkins "Total Syntheses Of (+)- and (−)-Syringolides 1 and 2" *Journal of Organic Chemistry* (1995), 60(22), 286-287; S. Sakuda, S. Tanaka, K. Mizuno, O. Sukcharoen, T. Nihira and Y. Yamada, "Biosynthetic studies on Virginiae butanolide A, a butyrolactone autoregulator from *Streptomyces*. II: Preparation of possible biosynthetic intermediates and conversion experiments in a cell-free system", *Journal of the Chemical Society. Perkin Transactions. I: Organic and Bio-organic Chemistry* (1972-1999) (1993), 19, 2308-2315; R. N. Lacey "Derivatives of acetoacetic acid. Part VI. A synthesis of 1:3-oxazine derivatives employing diketen" *J. Chem. Soc.*, 1954, 845-849). However, the use of dioxin-4-one has never been described.

This reaction step of the compound of formula (II) with dioxin-4-one (III), or a silyl derivative thereof, in the presence of a base is a regioselective furanone formation reaction. Specifically, the compound of formula (II) contains two carbonyl functions α and α' to the hydroxide. The cyclization reaction may thus potentially be performed on these two ketones. The regioselectivity of formation is dependent on the substitution of the dioxin-4-one. Generally, the furanone is predominantly formed in the para position of the exocyclic double bond, leading to the desired analog. In the only case where R represents a methyl group, a 50/50 mixture of the two regioisomers is obtained.

Typically, the step of reaction of the compound of formula (II) with the dioxin-4-one (III), or a silyl derivative thereof, in the presence of a base may be followed by one or more separation and optionally purification step(s). The separation may be, for example, a filtration, crystallization, precipitation, distillation, liquid-liquid extraction or chromatography step, whichever the case. The purification may be, for example, a recrystallization or chromatography step. In particular, the compound of formula (I) may be purified by chromatography on a column of silica in normal phase or reverse phase or by preparative high-performance liquid-phase chromatography (HPLC).

According to one particular mode of the invention, the reaction of the compound of formula (II) with dioxin-4-one (III), or a silyl derivative thereof, in the presence of a base is a monotope reaction.

The term "monotope reaction", more commonly known as a "one-pot reaction", means a reaction in several successive steps performed in the same reactor, without isolation of the intermediate products.

The base used in this reaction of the compound of formula (II) with the dioxin-4-one (III), or a silyl derivative thereof, may be chosen from chemical compounds known as "Lewis bases": these are chemical species of which one of the constituents contains one or more non-bonding or lone pairs of electrons on its valency shell. Typically, the base used in this reaction may be chosen from the group of tertiary amines, such as triethylamine (of chemical formula $Et_3N$), isopropyldiethylamine (of chemical formula $iPrNEt_2$), diisopropylethylamine (of chemical formula $iPr_2NEt$), tributylamine (of chemical formula $Bu_3N$), pyridine, N-methylpiperidine and N-methylmorpholine, DABCO (1,4-diazabicyclo[2.2.2]octane), DBU (1,8-diaza-bicyclo[5.4.0]undec-7-ene) but also from the group of inorganic bases such as $Na_2CO_3$, $K_2CO_3$, $Cs_2CO_3$, $NaHCO_3$ and $KHCO_3$.

Typically, the reaction of the compound of formula (II) with the dioxin-4-one (III), or a silyl derivative thereof, in the presence of a base may be performed in an organic solvent, or in a mixture of organic solvents, which may be chosen, for example, from nonprotic organic solvents, which are either apolar, such as toluene, benzene or xylene, or polar, such as 1,2-dichloroethane, dimethoxyethane, dimethyl sulfoxide (DMSO), N-methyl-2-pyrrolidone (NMP), dimethylformamide (DMF), or dimethylacetamide (DMA) in the limit in which the boiling point of said solvent is greater than 80° C. In addition, it is possible to use a drying product, for instance molecular sieves, in the reaction medium.

Typically, the reaction of the compound of formula (II) with the dioxin-4-one (III), or a silyl derivative thereof, in the presence of a base may be performed under hot conditions, preferably at a temperature above 80° C., and more preferably at a temperature of between 80° C. and 110° C., and at atmospheric pressure. The heating temperature may depend on the chosen solvent: it will be preferred to work at atmospheric pressure at a temperature below the boiling point of the solvent. For example, if the reaction is performed in toluene, the reaction temperature may be between 80° C. and 110° C., preferably between 90° C. and 105° C. and more preferentially between 95° C. and 100° C.

The dioxin-4-one (III) may be prepared according to processes known in the literature.

A first known literature process consists in preparing the dioxin-4-one from acid chloride or Weinreb amides, by condensation of the anion of tert-butyl acetate, followed by cyclization of the β-keto ester obtained in acidic medium in acetone. This first process is represented by the reaction scheme (A) below:

Reaction scheme A

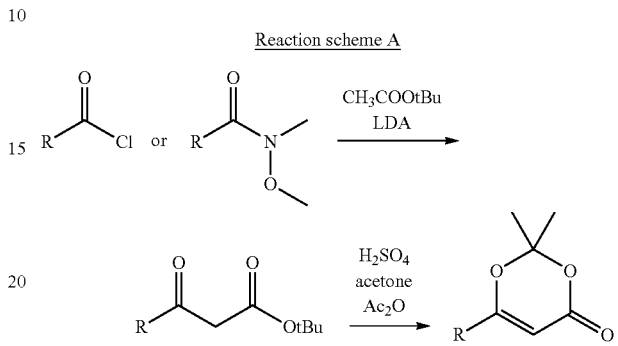

A second known literature process consists in preparing the dioxin-4-one by reacting the anion of methyldioxin-4-one with an electrophile of acid chloride or Weinreb amide type. This second process is represented in reaction scheme (B) below:

Reaction scheme B

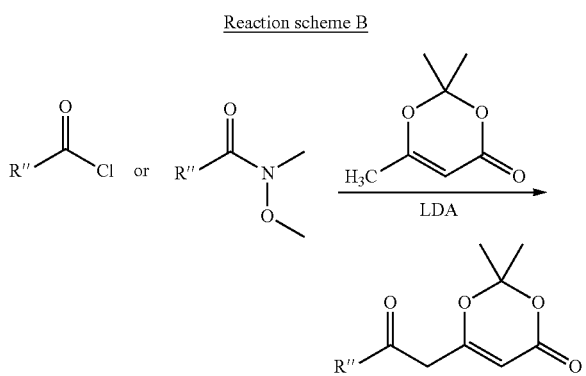

It is also possible to use acylbenzotriazole derivatives as described by Katritzky (*J. Org. Chem.* (2005), 70, 4854-4856), which are acid chloride equivalents.

The silyl derivative of the dioxin-4-one (III) may be prepared by silylation of a dioxin-4-one, according to the known literature processes.

The compound of formula (II) may be prepared according to the known literature processes.

According to one embodiment of the present invention, the compound of formula (II) is obtained by reacting a compound of formula (IV)

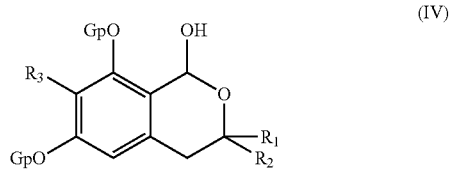

(IV)

or a similar compound,
with o-iodoxybenzoic acid, in the presence of an acid chosen from trifluoroacetic acid, p-toluenesulfonic acid, perchloric acid, hydrochloric acid and acetic acid. Preferably, the reaction of a compound of formula (IV) with an acid as described above is performed with o-iodoxybenzoic acid in the presence of trifluoroacetic acid.

According to the present invention, Gp denotes a protecting group for an alcohol function that may be deprotected under acidic conditions. The term "protecting group" typically refers to a functional group introduced into the molecule so as to prevent side reactions from taking place in the rest of the synthesis and/or to obtain a certain chemioselectivity. The Gp may be chosen from protecting groups for alcohol functions that may be deprotected under acidic conditions known to those skilled in the art, in particular those listed in the book "Protective Groups in Organic Synthesis" by T. W. Greene and P. G. M. Wuts. Typically, the Gp may be chosen from MOM, MEM, SEM, BOM, PMBOM, Bn, PMB, TMS, TBDMS. Preferably, the Gp is MOM.

MOM is the acronym for "methoxymethyl", which corresponds to the radical $CH_3—O—CH_2—$.

MEM is the acronym for "methoxyethyl", which corresponds to the radical $CH_3—O—CH_2—CH_2—$.

SEM is the acronym for "2-(trimethylsilyl)ethoxymethyl", which corresponds to the radical $SiMe_3-CH_2—CH_2—O—CH_2—$.

BOM is the acronym for "benzyloxymethyl", which corresponds to the radical $PhCH_2—OCH_2—$.

PMBOM is the acronym for "para-methoxybenzyloxymethyl", which corresponds to the radical $4-OMePhCH_2—OCH_2—$.

Bn is the acronym for "benzyl", which corresponds to the radical $PhCH_2—$.

PMB is the acronym for "para-methoxybenzyl", which corresponds to the radical $4-OMePhCH_2—$.

TMS is the acronym for "trimethylsilyl", which corresponds to the radical $Me_3Si—$.

TBDMS is the acronym for "tert-butyldimethylsilyl", which corresponds to the radical $tBuMe_2Si—$.

The term "similar compound" means compounds having a structure similar to that of the hemiacetal of formula (IV), which is a masked aldehyde form. The compounds similar to the hemiacetal of formula (IV) are, for example, free aldehydes.

In addition, the similar compounds are also the compounds of formula (IV) in which one or two protecting groups Gp have been replaced with a hydrogen. These similar compounds may be obtained by total or partial deprotection of the compounds of formula (IV). The deprotection is performed in acidic medium, according to the nature of the protecting group.

Typically, the similar compounds to the hemiacetal of formula (IV) are the compounds below:

acetal form

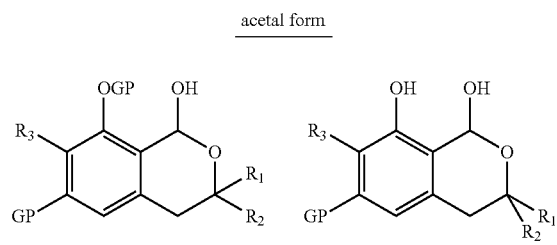

-continued

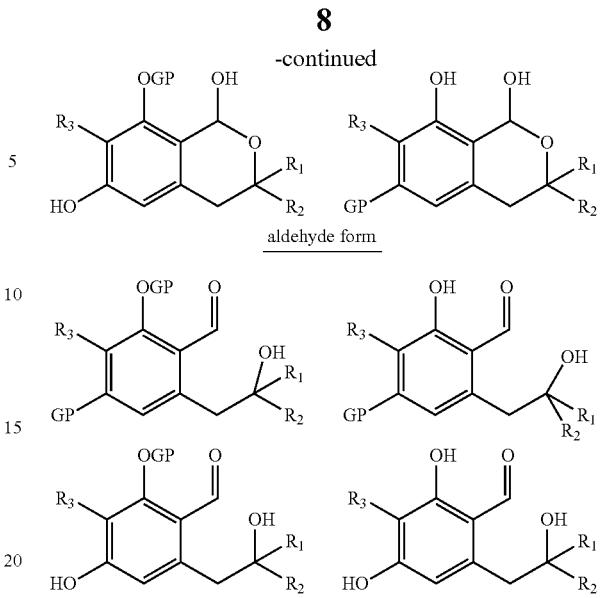

aldehyde form o-iodoxybenzoic acid, the acronym of which is IBX, is a multivalent iodine derivative. It is an oxidizing organic compound conventionally used for oxidizing alcohols to aldehydes. IBX is commercially available in a form stabilized with carboxylic acids such as benzoic acid or isophthalic acid. It may also be prepared via processes known to those skilled in the art, for example from 2-iodobenzoic acid, potassium bromide and sulfuric acid or from oxone.

Trifluoroacetic acid, the acronym of which is TFA, is a very strong carboxylic acid used in organic chemistry. It is commercially available, or may be synthesized by electrofluoration of acetic acid by means of a method known as the "Simmons method".

The reaction of a compound of formula (IV) with o-iodoxybenzoic acid in the presence of an acid as described above allows the deprotection of the alcohol functions protected with the groups Gp, followed by oxidation of the phenols obtained.

Typically, the reaction of the compound of formula (IV) with o-iodoxybenzoic acid in the presence of an acid as described above may be performed in an organic solvent, or in a mixture of organic solvents, which may be chosen in particular from chlorinated organic solvents, such as dichloromethane.

Typically, the reaction of the compound of formula (IV) with o-iodoxybenzoic acid in the presence of an acid as described above may be performed at room temperature and at atmospheric pressure.

According to one particular mode of the invention, the reaction of the compound of formula (IV) with o-iodoxybenzoic acid in the presence of an acid as described above is performed with an excess of acid. Preferably, between 2 and 50 equivalents and more preferably between 5 and 10 equivalents of acid may be used relative to the compound of formula (IV). Large excesses of acid are thus possible, but are unnecessary for the correct functioning of the reaction.

The compound of formula (IV) may be prepared according to the known literature processes.

According to one embodiment of the present invention, the compound of formula (IV) is obtained by reacting a compound of formula (V)

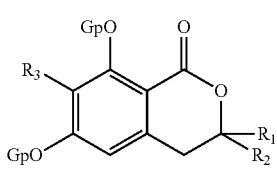

(V)

with diisobutylaluminum hydride.

Diisobutylaluminum hydride, the acronym of which is DIBAL-H, or commonly just DIBAL, is a reducing reagent that is widely used in organic chemistry.

In the reaction of the compound of formula (V) with diisobutylaluminum hydride, this reagent can reduce the lactone of the compound of formula (V) to the lactol in the compound of formula (IV).

Typically, the reaction of the compound of formula (V) with diisobutylaluminum hydride may be performed in an organic solvent, or in a mixture of organic solvents, which may be chosen in particular from organic solvents such as toluene, hexane, benzene, tetrahydrofuran and chlorinated solvents such as dichloromethane.

Typically, the reaction of the compound of formula (V) with diisobutylaluminum hydride may be performed under cold conditions, preferably at a temperature below −10° C. and more preferably at a temperature of −78° C., obtained, for example, in cardice, and at atmospheric pressure.

The compound of formula (V) may be prepared according to the known literature processes.

According to one embodiment of the present invention, the compound of formula (V) is obtained by protecting the alcohol functions of a compound of formula (VI)

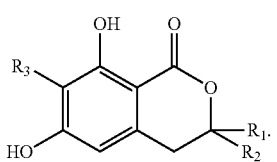

(VI)

Typically, the protection of the alcohol functions of a compound consists in reacting said compound, which contains alcohol functions, with a protecting reagent, which leads to the attachment of a protecting group to the alcohol functions. The protecting reagent is chosen as a function of the desired protecting group. As already stated hereinabove, the protecting groups that may be used here may be chosen from protecting groups for alcohol functions that may be deprotected under acidic conditions known to those skilled in the art, in particular those listed in the book "Protective Groups in Organic Synthesis" by T. W. Greene and P. G. M. Wuts, Wiley-Interscience Edts.

According to one embodiment of the present invention, the compound of formula (VI) may be protected by reaction with chloromethyl methyl ether, or CMME, also known as MOM-Cl, which corresponds to the compound CH$_3$—O—CH$_2$—Cl. Another embodiment consists in reacting dimethoxymethane in the presence of P$_2$O$_5$.

Typically, the protection reaction of the alcohol functions of a compound of formula (VI) may be performed in an organic solvent, or in a mixture of organic solvents, which may be chosen in particular from apolar organic solvents, such as toluene, hexane, benzene, ethyl acetate and chlorinated solvents such as dichloromethane.

In addition, it is possible to add a base, such as triethylamine, diisopropylethylamine and sodium hydride to the reaction medium for the protection reaction of the alcohol functions of a compound of formula (VI).

Typically, the protection reaction of the alcohol functions of a compound of formula (VI) may be performed, depending on the case, at room temperature, under cold conditions or under hot conditions, and at atmospheric pressure.

The compound of formula (VI) may be prepared according to the known literature processes.

According to one embodiment of the present invention, the compound of formula (VI) is obtained by reacting a compound of formula (VII)

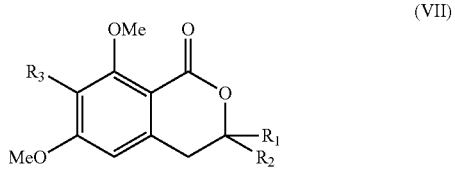

(VII)

with a Lewis acid.

The Lewis acid used as reagent with the compound of formula (VI) may be chosen from chemical compounds known as "Lewis acids": such an acid is a chemical species, of which one of the atoms constituting it has an electron deficiency, which makes it capable of accepting an electron pair, and thus of creating a covalent bond with a Lewis base. Typically, the Lewis acid used in this reaction may be chosen from the group consisting of aluminum trichloride (acronym AlCl$_3$), the aluminum trichloride/sodium iodide mixture (acronym AlCl$_3$/NaI), boron tribromide (acronym BBr$_3$), boron trichloride (acronym BCl$_3$), the trimethylsilyl chloride/sodium iodide mixture (acronym TMSCl/NaI), trimethylsilyl bromide (acronym TMSBr), trimethylsilyl iodide (acronym TMSI), ethanethiol (acronym EtSH) and benzenethiol (acronym PhSH).

Typically, the reaction of the compound of formula (VII) with a Lewis acid may be performed in an organic solvent, or in a mixture of organic solvents, which may be chosen, for example, from acetonitrile, dimethylformamide, dimethyl sulfoxide, N-methyl-2-pyrrolidone and chlorinated solvents such as dichloromethane.

Typically, the reaction of the compound of formula (VII) with a Lewis acid may be performed, depending on the case, at room temperature or under hot conditions, and at atmospheric pressure. For example, the reaction with aluminum trichloride in dichloromethane may be performed at the reflux point of the dichloromethane. If the reaction is performed with thiols, it may take place under hot conditions.

The compound of formula (VII) may be prepared according to the known literature processes.

According to one embodiment of the present invention, the compound of formula (VII) is obtained by reacting a compound of formula (VIII)

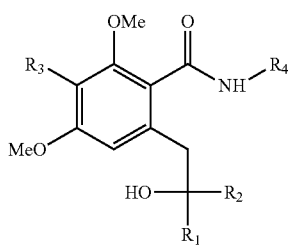

in which R4 represents a group chosen from isopropyl, ethyl and tert-butyl,
in acidic medium.

This reaction step of the compound of formula (VIII), which contains an alcohol function and an amide function, in acidic medium, is a lactonization, and leads to a release of isopropylamine.

Typically, the medium of this reaction of the compound of formula (VIII) may be acidic by adding one or more Brönsted acids, in particular those chosen from the group consisting of camphorsulfonic acid (acronym CSA), p-toluenesulfonic acid (acronym PTSA) and hydrochloric acid (acronym HCl).

For the purposes of the present invention, the term "in acidic medium" means that the acid present in the reaction medium is in excess relative to the product which will react. Typically, the reaction of the compound of formula (VIII) in acidic medium may be performed with an excess of 1.1 equivalents of acid relative to the compound of formula (VIII).

Typically, the reaction of the compound of formula (VIII) in acidic medium may be performed under hot conditions, typically at the reflux temperature of the reaction solvent, and at atmospheric pressure.

The compound of formula (VIII) may be prepared according to the known literature processes.

According to one embodiment of the present invention, the compound of formula (VIII) is obtained by reacting a compound of formula (IX)

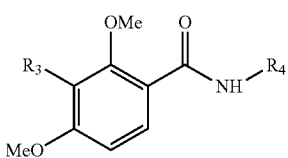

in which R4 represents a group chosen from isopropyl, ethyl and tert-butyl,
with an organolithium derivative or an organomagnesium derivative or a mixed aggregate, followed by reaction with a compound of formula (X)

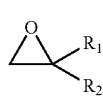

in which R1 and R2 are as described previously.

The reaction of a compound of formula (IX) with an organolithium derivative makes it possible to perform an organolithiation on the compound of formula (IX).

Typically, the organolithium derivative may be chosen from the group consisting of butyllithium (BuLi or nBuLi), tert-butyllithium (tBuLi), sec-butyllithium (sBuLi). Typically, the organomagnesium derivative may be isopropylmagnesium. Finally, typically, the mixed aggregate denotes the magnesium/lithium reagent mixture and it may be $Bu_3MgLi$.

According to the organolithium derivative or organomagnesium derivative or mixed aggregate used, in the reaction of the compound of formula (IX), the presence of a compound such as N,N,N',N'-tetramethylethylenediamine, the acronym of which is TMEDA, and whose role is to form stable complexes with metals, may be essential.

In a second stage, the lithiated derivative of the compound of formula (IX) is placed in contact with the epoxide of formula (X) to form the corresponding alcohol. Depending on the nature of the substituents R1 and R2, the epoxide of formula (X) may or may not be commercially available. If it is not commercially available, it may be prepared according to methods that are well known to those skilled in the art. The most common synthetic routes proceed via the oxidation of alkenes. For example, an appropriately selected alkene may be oxidized with atmospheric dioxygen over a silver catalyst. Another route consists in using a peracid to oxidize the appropriately selected alkene. The term "appropriately selected alkene" means the alkene containing the substituents R1 and R2 correctly located so as to form after oxidation the epoxide of formula (X) having the correct substituents R1 and R2.

Typically, the two reaction steps for the compound of formula (IX) with an organolithium derivative, and then with the compound of formula (X) may be performed in an organic solvent, or in a mixture of organic solvents, which may be chosen in particular from polar organic solvents, such as tetrahydrofuran and diethyl ether, and from apolar organic solvents, such as toluene, hexane or benzene.

Typically, the two steps of the reaction of the compound of formula (IX) with an organolithium derivative, and then with the compound of formula (X), may be performed at variable temperature, under cold conditions or at room temperature, typically between −100° C. and 25° C., and at atmospheric pressure.

The compound of formula (IX) may be prepared according to the known literature processes.

Typically, an amide such as the compound of formula (IX) may be prepared from the corresponding carboxylic acid, or its acid chloride or from any other similar derivative, in the presence of an amine.

According to one embodiment of the present invention, the compound of formula (IX) is obtained by reacting a compound of formula (XI)

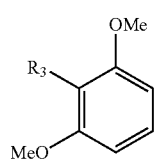

with an isocyanate of formula (XII)

in which R4 represents a group chosen from isopropyl, ethyl and tert-butyl,
in the presence of a Lewis acid.

The compound of formula (XI) is 1,3-dimethoxybenzene substituted in position 2 with a group R3. 1,3-Dimethoxybenzene is a commercial product. Its substitution in position 2 with a group R3 may be performed according to the standard methods known to those skilled in the art.

The compound of formula (XII) is an isocyanate, and is also a commercial product.

The Lewis acid used in this reaction of the compound of formula (XI) with the isocyanate of formula (XII) may be chosen from the chemical compounds known as "Lewis acids" as defined previously. Typically, the Lewis acid used in this reaction may be chosen from the group consisting of aluminum trichloride (formula $AlCl_3$), aluminum tribromide ($AlBr_3$), zinc chloride ($ZnCl_2$), zinc bromide ($ZnBr_2$), zinc iodide ($ZnI_2$), iron chloride ($FeCl_3$ or $FeCl_2$), iron bromide ($FeBr_3$ or $FeBr_2$), tin chloride ($SnCl_2$), tin bromide ($SnBr_2$), tin triflate ($Sn(OTf)_2$), indium chloride ($InCl_3$), indium bromide ($InBr_3$), indium triflate ($In(OTf)_3$), lanthanides in general, such as Sc, Hf, Y, Yb and Lu, triflates and bis- or tris-trifluoromethanesulfonamide $(NTf_3)_2$ or $(NTf_3)_3$ depending on the oxidation state of the metal, and bismuth or zirconium salts.

Typically, the reaction of the compound of formula (XI) with the isocyanate of formula (XII) in the presence of a Lewis acid may be performed in an organic solvent, or in a mixture of organic solvents, which may be chosen in particular from toluene, hexane, benzene, xylene, nitrobenzene, nitromethane, dichloromethane, chloroform and 1,2-dichloroethane.

Typically, the reaction of the compound of formula (XI) with the isocyanate of formula (XII) in the presence of a Lewis acid may be performed at room temperature and at atmospheric pressure.

In summary, a process is described herein for the total synthesis of compounds of formula (I) corresponding to reaction scheme (C) below:

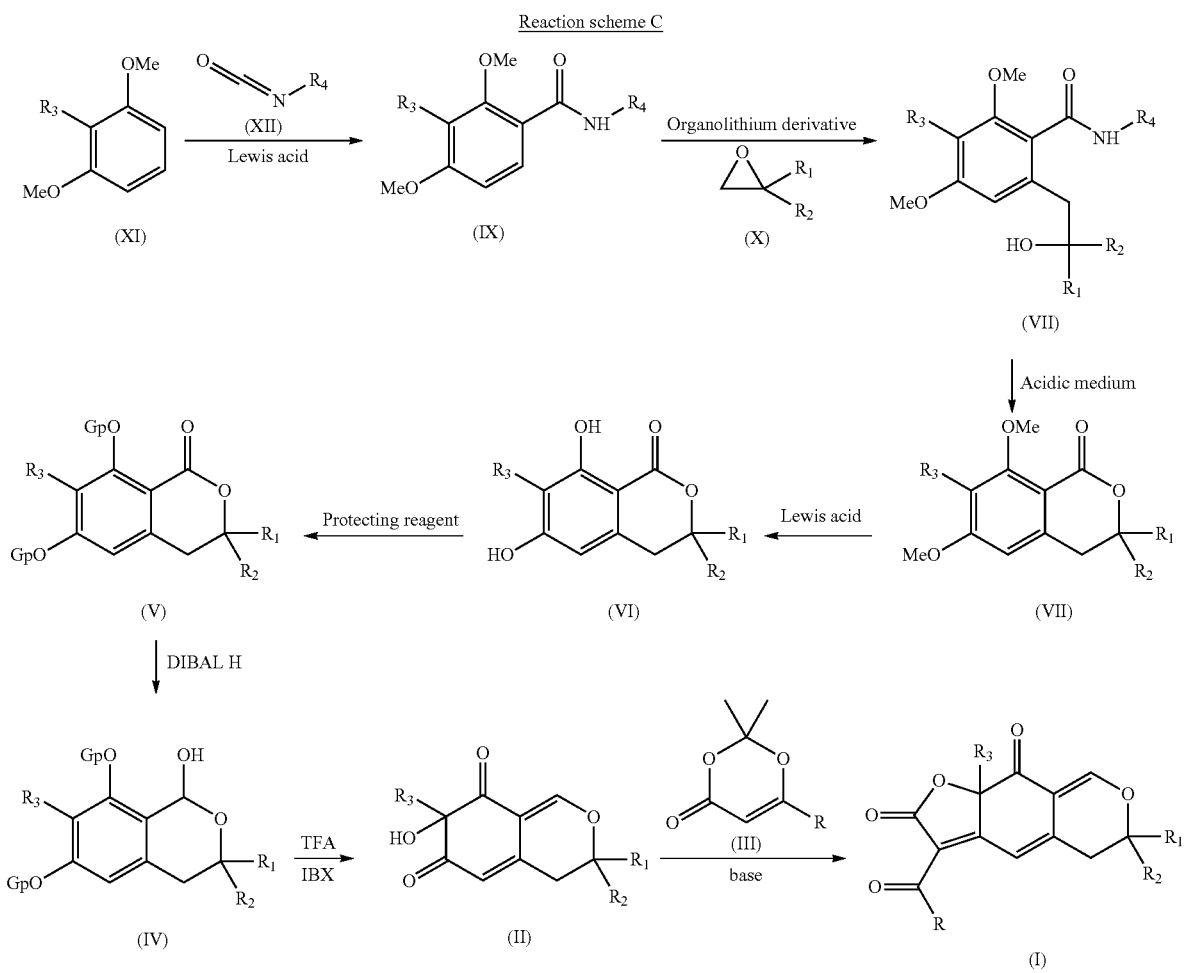

In general, all the intermediate chemical compounds involved in the process for synthesizing the compounds of formula (I) may be separated and optionally purified. Typically, one or more separation or purification step(s), or both consecutively, may be performed. The separation may be, for example, a filtration, crystallization, precipitation, distillation, liquid-liquid extraction or chromatography step. The purification may be, for example, a recrystallization or chromatography step. It is also possible to use the intermediate products without intermediate purification steps.

In addition, in general, most of the intermediate chemical compounds involved in the process for synthesizing the compounds of formula (I) contain one or more asymmetric centers. Determination of the relative configuration of these chemical compounds may be performed via any analytical technique known to those skilled in the art. Typically, measurement of the optical rotation may be used. The reaction steps described may lead to mixtures of enantiomers or of diastereoisomers. A person skilled in the art will know, if he desires, how to use efficient separation methods in order to separate the mixtures of enantiomers or of diastereoisomers, for example column chromatography on silica gel or purification by preparative HPLC. Moreover, the stereoselectivity of the reaction steps may also vary as a function of the operating conditions.

The Applicant has shown that the synthetic process according to the invention, when it is performed, can allow the synthesis of epicocconone analogs that have never been described previously.

The present invention thus also relates to the compounds of formula (I')

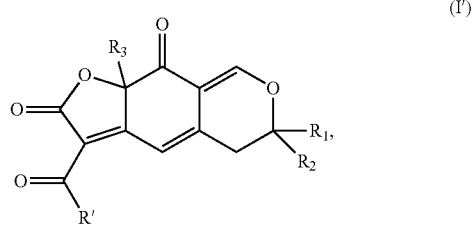

(I')

tautomers thereof, stereoisomers thereof and mixtures thereof, in which

R1, R2 and R3 are each independently a hydrogen, a halogen,
  a C1 to C20 alkyl chain, which may optionally comprise one or more heteroatoms chosen from O, N, S and P, which may be optionally substituted with one or more identical or different substituents chosen from a halogen and a hydroxyl, oxo, amino, amido, ether, ester or urea group,
  a C2 to C20 alkenyl chain, which may optionally comprise one or more heteroatoms chosen from O, N, S and P, which may be optionally substituted with one or more identical or different substituents chosen from a halogen and a hydroxyl, oxo, amino, amido, ether, ester or urea group, R' represents -A-C',
  A denoting a chemical bond or a linear or branched divalent radical, containing 1 to 20 carbon atoms, which may optionally comprise one or more heteroatoms chosen from O, N, S and P, and which may comprise one or more unsaturations, and which may be optionally substituted with one or more identical or different substituents chosen from a halogen, a hydroxyl group and an oxo group, and
  C' being a monocyclic or polycyclic group, which may optionally comprise one or more heteroatoms chosen from O, N, S and P, optionally containing one or more unsaturations and being optionally substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl chain]-O)$_n$—(C1 to C4 alkyl chain), n being 1 to 10.

In particular, the group R' may comprise rings, which was not the case for epicocconone itself and the analogs already described in the literature and produced from epicocconone isolated from a species of fungus.

According to one embodiment of the present invention, R1, R2 and R3 are each independently a hydrogen or a C1 to C20 alkyl chain or a C1 to C20 alkenyl chain, which may be optionally substituted with one or more identical or different substituents chosen from a halogen, a hydroxyl group and an oxo group. For example, R1, R2 and R3 are each independently a hydrogen or an unsubstituted C1 to C6 alkyl chain, such as a methyl, an ethyl, a propyl, an n-butyl, an sec-butyl and a tert-butyl. For example, R1, R2 and R3 are each independently a hydrogen or a methyl.

According to one embodiment of the present invention, R' represents -A-C' in which C' is a monocyclic or polycyclic group containing only carbon atoms, optionally containing one or more unsaturations and possibly being substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl chain]-O)$_n$—(C1 to C4 alkyl chain), n being 1 to 10.

Typically, C' may be a phenyl group, which may optionally be substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl chain]-O)$_n$—(C1 to C4 alkyl chain), n being 1 to 10. Preferably, C' may be a phenyl group that is unsubstituted or substituted with a hydroxyl, methyloxy, ethyloxy, propyloxy, methyloxyethyloxyethyloxy, methylamino or dimethylamino group.

Typically, C' may also be a polycyclic group comprising only carbon atoms, in particular a group chosen from biphenyl, naphthyl and anthracenyl groups, which may be optionally substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl chain]-O)$_n$—(C1 to C4 alkyl chain), n being 1 to 10. Preferably, C' may also be a biphenyl, naphthyl or anthracenyl group, which is unsubstituted or substituted with a hydroxyl, methyloxy, ethyloxy, propyloxy, methyloxyethyloxyethyloxy, methylamino or dimethylamino group.

According to another embodiment of the present invention, R' represents -A-C' in which C' is a monocyclic or polycyclic group comprising one or more heteroatoms chosen from N, O, S and P, optionally containing one or more unsaturations and possibly being substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl]-O)$_n$—(C1 to C4 alkyl), n being 1 to 10.

Typically, C' may be a monocyclic group comprising one or more heteroatoms chosen from N, O and S, such as furyl, oxiranyl, 2H-pyranyl, 4H-pyranyl, thiophenyl, pyrrolyl, pyrrolidinyl, pyrazolyl, pyrazolydinyl, imidazolyl, imidazolyl, imidazolidinyl, pyridinyl, piperidinyl, pyrazinyl, piperazinyl, pyrimidinyl, para-thiazinyl and morpholinyl, each of these groups possibly being substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl]-O)$_n$—(C1 to C4 alkyl), n being 1 to 10. Preferably, C' may be a monocyclic group comprising one or more heteroatoms chosen from N, O and S, which is unsubstituted or substituted with a hydroxyl, methyloxy, ethyloxy, propyloxy, methyloxyethyloxyethyloxy, methylamino or dimethylamino group.

Typically, C' may also be a polycyclic group comprising one or more heteroatoms chosen from N, O and S, such as 2H-chromenyl, benzofuryl, benzothiophenyl, indolyl, purinyl, benzothiazolyl, benzimidazolyl, quinolinyl and phenothiazinyl groups, each of these groups possibly being substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkylamino) type of formula —O—([C1 to C4 alkyl chain]-O)$_n$—(C1 to C4 alkyl chain), n being 1 to 10. Preferably, C' may be a polycyclic group comprising one or more heteroatoms chosen from N, O and S, which is unsubstituted or substituted with a hydroxyl, methyloxy, ethyloxy, propyloxy, methyloxyethyloxyethyloxy, methylamino or dimethylamino group.

In addition, according to one embodiment of the present invention, R' represents -A-C' in which A represents a chemical bond. Preferably, the compound of formula (I') may be chosen from the compounds of formulae (Ia) to (Ih) below:

| | Formula | Name | R1 | R2 | R3 | R |
|---|---|---|---|---|---|---|
| Ia | | 3-benzoyl-6,9a-dimethyl-5,6-dihydro-9aH-furo[3,2-g]isochromene-2,9-dione | H | Me | Me | Ph |
| Ib | | 3-(4-methoxybenzoyl)-6,9a-dimethyl-5,6-dihydro-9aH-furo[3,2-g]isochromene-2,9-dione | H | Me | Me | p-OMe Ph |
| Ic | | 3-(furan-2-carbonyl)-6,9a-dimethyl-5,6-dihydro-9aH-furo[3,2-g]isochromene-2,9-dione | H | Me | Me | 2-furyl |

-continued

| Formula | | Name | R1 | R2 | R3 | R |
|---|---|---|---|---|---|---|
| Id | (structure) | 3-(2-naphthoyl)-6,9a-dimethyl-5,6-dihydro-9aH-furo[3,2-g]isochromene-2,9-dione | H | Me | Me | 2-naphthyl |
| Ie | (structure) | 3-(4-(2-(2-methoxyethoxy)ethoxy)benzoyl)-6,9a-dimethyl-5,6-dihydro-9aH-furo[3,2-g]isochromene-2,9-dione | H | Me | Me | 4-(2-(2-methoxyethoxy)ethoxy)phenyl |
| If | (structure) | 3-(2-methoxybenzoyl)-6,9a-dimethyl-5,6-dihydro-9aH-furo[3,2-g]isochromene-2,9-dione | H | Me | Me | 2-methoxyphenyl |
| Ig | (structure) | 3-(2-hydroxybenzoyl)-6,9a-dimethyl-5,6-dihydro-9aH-furo[3,2-g]isochromene-2,9-dione | H | Me | Me | 2-hydroxyphenyl |
| Ih | (structure) | 3-(4-methoxybenzoyl)-6,6,9a-trimethyl-5,6-dihydro-9aH-furo[3,2-g]isochromene-2,9-dione | Me | Me | Me | 4-methoxyphenyl |

According to another embodiment of the present invention, R' represents -A-C' in which A is a linear or branched divalent radical, containing 1 to 20 carbon atoms, which may optionally comprise one or more heteroatoms chosen from O, N, S and P, and which may comprise one or more unsaturations, and may be optionally substituted with one or more identical or different substituents chosen from a halogen, a hydroxyl group and an oxo group. Preferably, A is a linear or branched divalent radical containing 1 to 5 carbon atoms comprising zero, one or two unsaturations, and being unsubstituted or substituted with one or more identical or different substituents chosen from a hydroxyl group and an oxo group. Even more preferably, A comprises a 1,3-diketone structure which is in the keto-enol form.

Preferably, the compound of formula (I') may be chosen from the compounds of formulae (Ii) to (Im) below, or from compounds (Ii) to (Io) below:

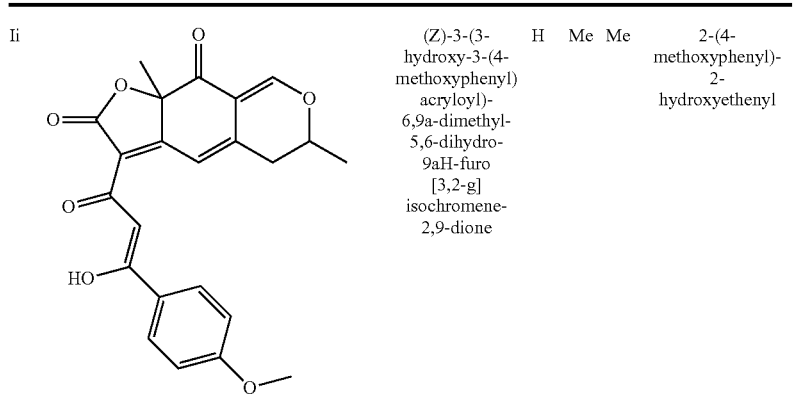

Ii — (Z)-3-(3-hydroxy-3-(4-methoxyphenyl)acryloyl)-6,9a-dimethyl-5,6-dihydro-9aH-furo[3,2-g]isochromene-2,9-dione — H  Me  Me — 2-(4-methoxyphenyl)-2-hydroxyethenyl

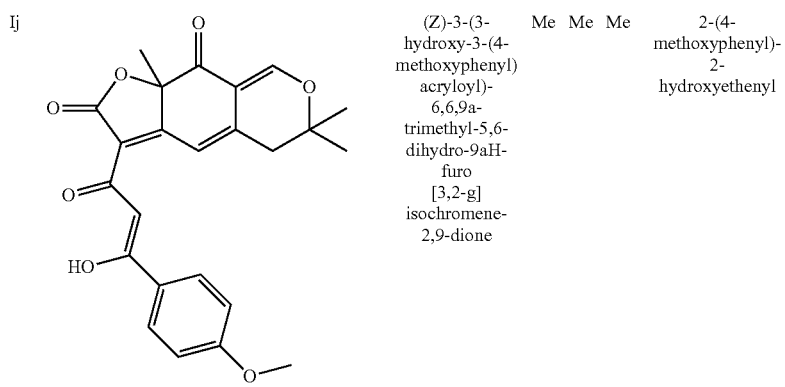

Ij — (Z)-3-(3-hydroxy-3-(4-methoxyphenyl)acryloyl)-6,6,9a-trimethyl-5,6-dihydro-9aH-furo[3,2-g]isochromene-2,9-dione — Me  Me  Me — 2-(4-methoxyphenyl)-2-hydroxyethenyl

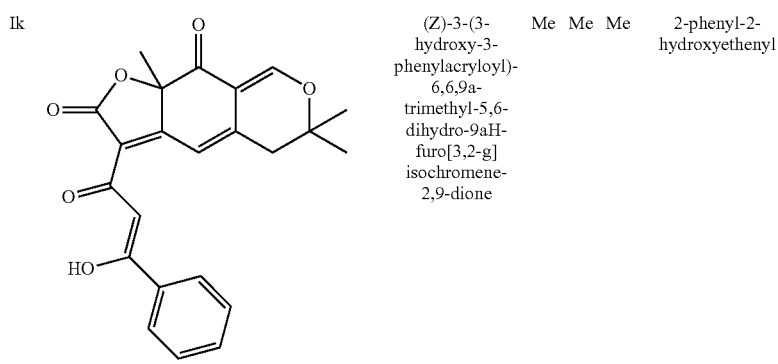

Ik — (Z)-3-(3-hydroxy-3-phenylacryloyl)-6,6,9a-trimethyl-5,6-dihydro-9aH-furo[3,2-g]isochromene-2,9-dione — Me  Me  Me — 2-phenyl-2-hydroxyethenyl -continued

| | | | R1 | R2 | R3 | R |
|---|---|---|---|---|---|---|
| Il | (structure) | 3-(3-(4-methoxyphenyl)-2-methyl-3-oxopropanoyl)-6,6,9a-trimethyl-5,6-dihydro-9aH-furo[3,2-g]isochromene-2,9-dione | Me | Me | Me | 2-[1-(4-methoxyphenyl)-1-oxo-2-methyl)propyl |
| Im | (structure) | 6,6,9a-trimethyl-3-(2-methyl-3-oxo-3-phenylpropanoyl)-5,6-dihydro-9aH-furo[3,2-g]isochromene-2,9-dione | Me | Me | Me | 2-(1-phenyl-1-oxo-2-methyl)propyl |
| In | (structure) | 3-[3-(6-chloro-pyridin-3-yl)-1-hydroxy-3-oxopropenyl]-6,6,9a-trimethyl-5,6-dihydro-9aH-furo[3,2-g]isochromene-2,9-dione | Me | Me | Me | 2-(6-chloro-pyridin-3-yl)-2-hydroxyethenyl) |
| Io | (structure) | 3-(1-hydroxy-3-naphtalen-2-yl-3-oxopropenyl)-6,6,9a-trimethyl-5,6-dihydro-9aH-furo[3,2-g]isochromene-2,9-dione | Me | Me | Me | 2-[(2-naphthyl)-2-hydroxyethenyl) |

Preferably, the compound of formula (I') is chosen from the compounds of formulae (Ii), (Ij) and (Ik).

Relative to a process proceeding via the isolation of epicocconone from a species of fungus, the process for synthesizing compounds of formula (I) as described previously according to the invention has the advantage of being simple and adaptable to the synthesis of a very wide variety of epicocconone analogs.

The ability to choose with great liberty and great ease the nature of the substituents R1, R2, R3 and R is an advantage:

for example, modification of these substituents relative to epicocconone makes it possible to modulate the emission and absorption wavelengths of the compound. It is thus possible to obtain a compound in which the Stokes' shift (difference between the absorption wavelength and the emission wavelength) is equivalent to or greater than that of natural epicocconone.

The compounds obtained according to the process for synthesizing the compounds of formula (I) according to the invention, and the compounds of formula (I') according to the invention, have the particular feature of having the epicocconone backbone and, preferably, said compounds are epicocconone analogs. Epicocconone analogs may have the same advantageous properties as the natural molecule. Thus, the epicocconone analogs according to the invention may have the same uses as epicocconone itself. Some of these uses have already been described in detail in international patent applications WO 01/81351, WO 2004/085 546 and WO 2007/051 256, and in the following publications:

J. A. Mackintosh, H.-Y. Choi, S.-H. Bae, D. A. Veal, P. J. Bell, B. C. Ferrari, D. D. Van Dyk, N. M. Verrills, Y.-K. Paik, and P. Karuso, "A fluorescent natural product for ultra sensitive detection of proteins in one-dimensional and two-dimensional gel electrophoresis", *Proteomics* (2003), 3(12), 2273-2288.

D. R. Coghlan, J. A. Mackintosh and P. Karuso, "Mechanism of Reversible Fluorescent Staining of Protein with Epicocconone", *Organic Letters* (2005), 7(12), 240 1-2404.

J. A. Mackintosh, D. A. Veal and P. Karuso, "Fluoroprofile, a fluorescence-based assay for rapid and sensitive quantitation of proteins in solution" *Proteomics* (2005), 5(18), 4673-4677.

H.-Y. Choi, D. A. Veal and P. Karuso, "Epicocconone, a new cell-permeable long Stokes' shift fluorescent stain for live cell imaging and multiplexing", *Journal of Fluorescence* (2006), 16(4), 475-482.

C. M. Nock, M. S. Ball, I. R. White, J. M. Skehel, L. Bill and P. Karuso, "Mass spectrometric compatibility of Deep Purple and SYPRO Ruby total protein stains for high-throughput proteomics using large-format two-dimensional gel electrophoresis", *Rapid Communications in Mass Spectrometry* (2008), 22(6), 88 1-886.

P. Karuso, A. S. Crawford, D. A. Veal, G. B. I. Scott, and H.-Y. Choi, "Real-Time Fluorescence Monitoring of Tryptic Digestion in Proteomics", *Journal of Proteome Research* (2008), 7(1), 361-366.

The present invention also relates to the use of a compound obtained according to the process for synthesizing the compounds of formula (I) according to the invention, or a compound of formula (I') according to the invention, as a fluorescent dye or marker.

According to one embodiment, this use intervenes in a technique for staining, marking and/or detecting organic molecules.

The epicocconone analogs of formulae (I) and (I') are preferably not fluorescent in aqueous solution, but they may be capable of interacting with an organic compound to produce an intense fluorescent coloration.

According to one embodiment, the epicocconone analogs of formulae (I) and (I') interact with proteins to produce a fluorescent adduct that may be excited with standard UV radiation, the wavelength of which is between 300 and 560 nm. Under excitation, the fluorescent adduct may emit radiation over a wide range of wavelength values, allowing the protein adduct to be detected (see reaction scheme D).

Reaction scheme D

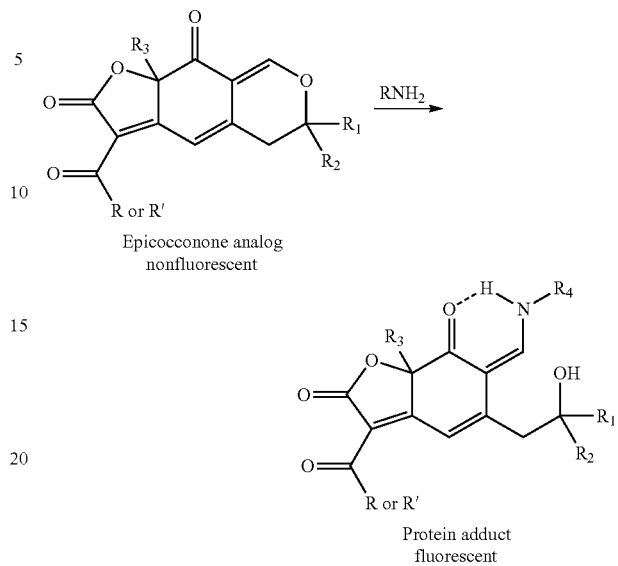

Epicocconone analog
nonfluorescent

Protein adduct
fluorescent

Thus, the present invention also relates to a method for the fluorescently staining of an organic molecule, comprising the placing of a compound obtained according to the process for synthesizing the compounds of formula (I) according to the invention, or a compound of formula (I') according to the invention, in contact with said organic molecule so as to covalently bond said compound to said organic molecule.

According to one preferred embodiment, said organic molecule may be chosen from a protein, a peptide, a sugar, a nucleic acid, a molecule constituting the wall of a cell and a detergent, or the organic molecule is included in an antibody or in a cell.

Other characteristics and advantages of the invention will emerge on reading the nonlimiting and purely illustrative examples that follow, taken in combination with the attached drawing which illustrates the photobleaching of compounds according to the invention.

EXAMPLES

Example 1

Synthesis of the Reaction Intermediates

1) Synthesis of
N-isopropyl-2,4-dimethoxy-3-methyl-benzamide
(IX)

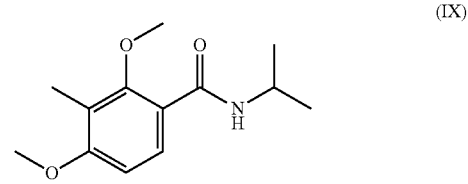

3.04 g (20 mmol, 1 eq.) of dimethoxytoluene and 2.80 g (21 mmol, 1.05 eq.) of $AlCl_3$ are dissolved in 20 mL of $CH_2Cl_2$ in a dried round-bottomed flask under argon. 2.36 mL (25 mmol, 1.25 eq.) of isopropyl cyanate are then added to the reaction medium at room temperature. After 10 hours, the reaction is hydrolyzed at 0° C. by adding saturated NH₄Cl solution.

After extraction with CH₂Cl₂, the organic phase is washed with 1N HCl solution and then with saturated NaHCO₃ solution. The organic phase is then dried with MgSO₄, filtered and concentrated under vacuum. After purification by chromatography on silica using a cyclohexane/ethyl acetate mixture (8:2), 4.50 g (95%) of amide (IX) are obtained.

Analyses:

¹H NMR (300 MHz, CDCl₃) δ ppm: 1.25 (d, J=6.5 Hz, 6H, 2×CH₃), 2.15 (s, 3H, CH₃), 3.73 (s, 3H, CH₃), 3.86 (s, 3H, CH₃), 4.26-4.37 (m, 1H, CH), 6.72 (d, J=8.7 Hz, 1H, CH$_{ar}$), 7.68 (d, J=5.6 Hz, 1H, NH), 7.94 (d, J=8.8 Hz, 1H, CH$_{ar}$).

¹³C NMR (75 MHz, CDCl₃) δ ppm: 9.1, 23.2, 41.4, 56.0, 61.5, 106.7, 119.4, 119.8, 130.2, 157.5, 161.3, 164.8.

2) Synthesis of 6-(2-hydroxypropyl)-N-isopropyl-2,4-di-methoxy-3-methylbenzamide (VIIIa)

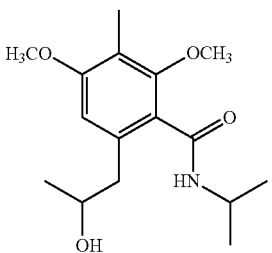

(VIIIa)

4.74 g (20 mmol, 1 eq.) of amide (IX) and 6.1 mL (40 mmol, 2 eq.) of TMEDA are dissolved in 200 mL of THF in a dried round-bottomed flask under argon. The medium is then placed at −78° C. 33.9 mL (44 mmol, 2.2 eq.) of t-BuLi (1.3M as a solution in hexane) are then added and the solution is immediately warmed to −15° C. Once the red/orange coloration has appeared, the medium is cooled to −78° C. 1.43 mL (20 mmol, 1 eq.) of propylene oxide are then added dropwise. Once the addition is complete, the medium is warmed rapidly to −10° C. The solution is then slowly warmed to room temperature over 1 hour 30 minutes. A second addition of propylene oxide (1 eq.) is made if necessary (monitoring of the conversion by TLC). After 30 minutes, the reaction is hydrolyzed by addition of 100 mL of water.

After extraction with CH₂Cl₂, the organic phase is washed with saturated NH₄Cl solution and then with saturated NaHCO₃ solution. The organic phase is then dried with MgSO₄, filtered and concentrated under vacuum. After purification by chromatography on silica, using a cyclohexane/ethyl acetate mixture (7:3), 5.9 g (82%) of amido alcohol (VIIIa) are obtained.

Analyses:

¹H NMR (300 MHz, CDCl₃) δ ppm: 1.22-1.31 (3d, 9H, CH₃), 2.10 (s, 3H, CH₃), 2.71 (dd, J=8.4 Hz and J=13.5 Hz, 1H, CH), 2.80 (dd, J=13.6 Hz and J=3.6 Hz, 1H, CH), 3.70 (s, 3H, CH₃), 3.83 (s, 3H, CH₃), 3.99 (bs, 1H, CH), 4.17-4.33 (m, 1H, CH), 4.98 (s, 1H, O—H), 6.26 (d, J=8 Hz, 1H, N—H), 6.57 (s, 1H, CH$_{ar}$).

¹³C NMR (75 MHz, CDCl₃) δ ppm: 8.9, 22.7, 23.0, 24.7, 42.2, 43.1, 55.9, 62.1, 69.0, 108.6, 118.3, 123.2, 138.2, 156.2, 159.5, 167.7.

3) Synthesis of 6-(2-hydroxy-2-methylpropyl)-N-isopropyl-2,4-dimethoxy-3-methylbenzamide (VIIIb)

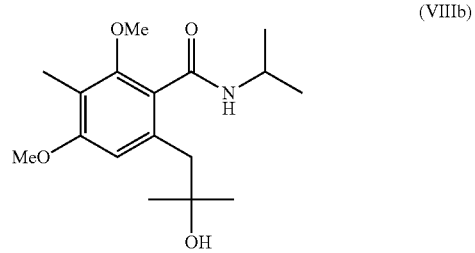

(VIIIb)

Procedure similar to (VIIIa). Yield=75%

Analyses:

¹H NMR (300 MHz, CDCl₃) δ ppm: 1.24 (d, J=6.57 Hz, 6H, CH₃), 1.30 (s, 6H, CH₃), 2.10 (s, 3H, CH₃), 2.79 (s, 2H, CH₂), 3.70 (s, 3H, CH₃), 3.83 (s, 3H, CH₃), 4.24-4.31 (m, 1H, CH), 5.68 (s, 1H, OH), 6.25 (d, J=7.35 Hz, 1H, NH), 6.48 (s, 1H, CH$_{ar}$).

¹³C NMR (75 MHz, CDCl₃) δ ppm: 8.7, 22.6, 30.4, 42.0, 46.7, 55.8, 62.0, 69.3, 110.0, 118.3, 123.1, 137.2, 156.2, 158.9, 167.8.

4) Synthesis of 6,8-dimethoxy-3,7-dimethylisochroman-1-one (VIIa)

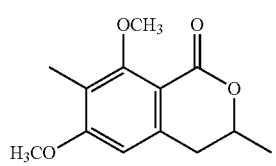

(VIIa)

4.05 g (14 mmol, 1 eq.) of amido alcohol (VIIIa) and 3.68 g of CSA (15.4 mmol, 1.1 eq.) are dissolved in 150 mL of toluene in a dried round-bottomed flask under argon. The toluene is then brought to reflux. After two hours, the reaction is hydrolyzed with 50 mL of H₂O.

After extraction with ethyl acetate, the organic phase is washed with saturated NH₄Cl solution and then with saturated NaHCO₂ solution. The organic phase is then dried over MgSO₄, filtered and concentrated under vacuum. The product is then precipitated from a minimum volume of cyclohexane. 3.02 g (92%) of lactone (VIIa) are obtained.

Analyses:

¹H NMR (300 MHz, CDCl₃) δ ppm: 1.47 (d, J=6 Hz, 3H, CH₃), 2.13 (s, 3H, CH₃), 2.71 (dd, J=3.4 Hz and J=15.8 Hz, 1H, CH), 2.80 (dd, J=10.6 Hz and J=16.2 Hz, 1H, CH), 3.85 (s, 3H, CH₃), 3.87 (s, 3H, CH₃), 4.48-4.59 (m, 1H, CH), 6.44 (s, 1H, CH).

¹³C NMR (75 MHz, CDCl₃) δ ppm: 8.6, 20.8, 36.3, 55.8, 61.6, 73.9, 104.6, 110.7, 120.3, 140.4, 161.4, 162.4, 162.8.

5) Synthesis of 6,8-dimethoxy-3,3,7-trimethylisochroman-1-one (VIIb)

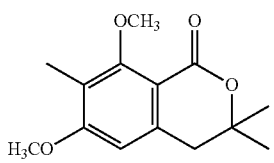
(VIIb)

Procedure similar to (VIIa), Yield=75%
Analyses:
$^1$H NMR (300 MHz, CDCl$_3$) δ ppm: 1.34 (s, 6H, CH$_3$), 2.07 (s, 3H, CH$_3$), 2.86 (s, 2H, CH$_2$), 3.76 (s, 3H, CH$_3$), 3.82 (s, 3H, CH$_3$), 6.40 (s, 1H, CH$_{ar}$).
$^{13}$C NMR (75 MHz, CDCl$_3$) δ ppm: 8.5, 27.1, 40.6, 55.7, 61.4, 79.0, 105.3, 110.5, 120.1, 139.1, 161.1, 162.1, 162.4.

6) Synthesis of 6,8-dihydroxy-3,7-dimethylisochroman-1-one (VIa)

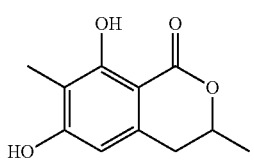
(VIa)

3.02 g (13 mmol, 1 eq.) of lactone (VIIa) and 17.33 g of AlCl$_2$ (130 mmol, 10 eq.) are dissolved in 200 mL of dichloromethane in a dried round-bottomed flask under argon. The solvent is then brought to reflux. After 16 hours, the reaction is hydrolyzed with 200 mL of 1N HCl at 0° C.

After separating out the organic phase, the aqueous phase is re-extracted with 2×100 mL of EtOAc. The organic phase is then dried over MgSO$_4$, filtered and evaporated under vacuum. 2.71 g (100%) of pure product are then obtained after precipitation from a minimum amount of dichloromethane.
Analyses:
$^1$H NMR (300 MHz, CDCl$_3$) δ ppm: 1.24 (d, J=6.27 Hz, 3H, CH$_3$), 2.12 (s, 3H, CH$_3$), 2.80-2.85 (m, 2H, CH$_2$), 4.60-4.71 (m, 1H, CH), 5.43 (s, 1H, OH), 6.20 (s, 1H, CH$_{ar}$), 11.48 (s, 1H, OH).
$^{13}$C NMR (75 MHz, CDCl$_3$) δ ppm: 7.7, 21.1, 34.9, 76.0, 101.8, 105.9, 110.9, 138.4, 160.3, 162.6, 170.6.

7) Synthesis of 6,8-dihydroxy-3,3,7-trimethylisochroman-1-one (VIb)

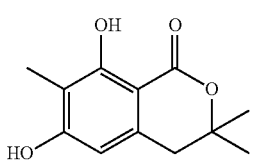
(VIb)

Procedure similar to (VIa). Yield=78%
$^1$H NMR (300 MHz, CDCl$_3$) δ ppm: 1.40 (s, 6H, CH$_3$), 2.01 (s, 3H, CHO, 2.91 (s, 2H, CH$_2$), 6.26 (s, 1H, CH$_{ar}$), 7.76 (s, 1H, OH), 11.60 (s, 1H, OH).
$^{13}$C NMR (75 MHz, CDCl$_3$) δ ppm: 8.4, 27.9, 39.8, 83.2, 101.9, 107.8, 110.9, 139.4, 163.0, 163.4, 171.3.

8) Synthesis of 6,8-bis(methoxymethyloxy)-3,7-dimethylisochroman-1-one (Va)

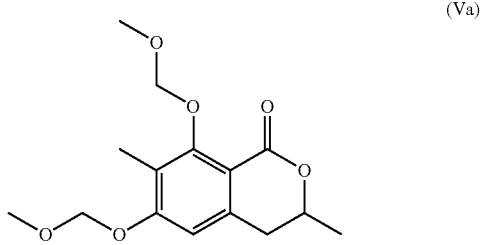
(Va)

2.6 g (12.7 mmol, 1 eq.) of diphenol (VIa) are dissolved in 250 mL of THF in a dried round-bottomed flask under argon. 660 mg of NaH (65 mmol, 5 eq.) and 14.8 mL of a 2.1N solution of MOMCl in toluene (31 mmol, 3 eq.) are added at room temperature. After 30 minutes, the reaction is hydrolyzed by adding 50 mL of H$_2$O.

After adding 100 mL of saturated NH$_4$Cl solution, the aqueous phase is extracted with 2×100 mL of ethyl acetate. The organic phase is then washed with 100 mL of saturated NaCl solution. The organic phase is then dried over MgSO$_4$, filtered and concentrated under vacuum. After purification by chromatography on silica, using a cyclohexane/ethyl acetate mixture (65:35), 3.08 g (98%) of lactone (Va) are obtained.

Analyses:
$^1$H NMR (300 MHz, CDCl$_3$) δ ppm: 1.24 (d, J=6.39 Hz, 3H, CH$_3$), 2.20 (s, 3H, CH$_3$), 2.84 (m, 2H, CH$_2$), 3.48 (s, 3H, CH$_3$), 3.60 (s, 3H, CH$_3$), 4.54 (s, 1H, CH), 5.06 (dd, J=6.6 Hz, 1H, CH), 5.13 (dd, J=6.6 Hz, 1H, CH), 5.22 (dd, J=6.8 Hz, 2H, CH$_2$), 6.70 (s, 1H, CH$_{ar}$).
$^{13}$C NMR (75 MHz, CDCl$_3$) δ ppm: 9.8, 21.0, 36.5, 56.7, 57.9, 74.4, 94.4, 101.7, 108.1, 111.5, 121.6, 140.4, 159.6, 160.1, 163.5.

9) Synthesis of 6,8-bis(methoxymethyloxy)-3,3,7-trimethylisochroman-1-one (Vb)

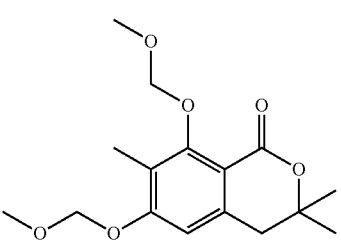
(Vb)

Procedure similar to (Va). Yield=75%
Analyses:
$^1$H NMR (300 MHz, CDCl$_3$) δ ppm: 1.31 (s, 6H, CH$_3$), 2.12 (s, 3H, CH$_3$), 2.82 (s, 2H, CH$_2$), 3.39 (s, 3H, CH$_3$), 3.50 (s, 3H, CH$_3$), 5.00 (s, 2H, CH$_2$), 5.15 (s, 2H, CH$_2$), 6.61 (s, 1H, CH$_{ar}$).

$^{13}$C NMR (75 MHz, CDCl$_3$) δ ppm: 9.3, 26.7, 40.3, 56.2, 57.4, 79.1, 94.0, 101.3, 108.5, 110.9, 121.0, 138.7, 158.9, 159.8, 162.3.

10) Synthesis of 6,8-bis(methoxymethyloxy)-3,7-dimethylisochroman-1-ol (IVa)

(IVa)

588 mg of lactone (Va) (2 mmol, 1 eq.) are dissolved in 20 mL of toluene in a 50 mL round-bottomed flask dried under argon. At −78° C., 3.1 mL of a 0.87 M solution of DIBAl-H in toluene (2.6 mmol, 1.3 eq.) are added. After 1 hour, the reaction is hydrolyzed by adding 50 mL of H$_2$O.

The product is extracted from the reaction medium with 50 mL of EtOAc and a further wash with 1N HCl is performed. Two washes with saturated NaCl solution are then performed and the organic phase is dried over MgSO$_4$, filtered and reduced under vacuum. 592 mg (100%) of lactol (IVa) are obtained without any purification.

Analyses:

$^1$H NMR (300 MHz, CDCl$_3$) δ ppm: 1.34 (d, J=6.21 Hz, 3H, CH$_3$), 2.14 (s, 3H, CH$_3$), 2.61 (m, 2H, CH$_2$), 3.47 (s, 3H, CH$_3$), 3.61 (s, 3H, CH$_3$), 3.62 (d, J=2.8 Hz, OH), 4.40-4.47 (s, 1H, CH), 5.03 (dd, J=2.5 Hz, 2H, CH$_2$), 5.18 (s, 2H, CH$_2$), 5.17 (d, J=2.85 Hz, 1H, CH), 6.65 (s, 1H, CH$_{ar}$).

$^{13}$C NMR (75 MHz, CDCl$_3$) δ ppm: 10.2, 21.6, 35.8, 56.4, 57.8, 63.2, 89.3, 94.8, 100.2, 110.13, 118.8, 123.3, 133.5, 154.8, 156.4.

11) Synthesis of 6,8-bis(methoxymethyloxy)-3,3,7-trimethylisochroman-1-ol (IVb)

(IVb)

Procedure similar to (Iva). Yield=99%

Analyses:

$^1$H NMR (300 MHz, CDCl$_3$) δ ppm: 1.23 (s, 3H, CH$_3$), 1.47 (s, 3H, CH$_3$), 2.2 (s, 3H, CH$_3$), 2.65 (d, J=15.5 Hz, 1H, CH), 2.65 (d, J=15.5 Hz, 1H, CH), 3.49 (s, 3H, CH$_3$), 3.61 (s, 3H, CH$_3$), 4.13 (s, 1H, OH), 5.01-5.07 (dd, J=2.7 Hz, 2H, CH$_2$), 5.19 (s, 2H, CH$_2$), 6.24 (d, 1H, CH), 6.69 (s, 1H, CH$_{ar}$).

12) Synthesis of 7-hydroxy-3,7-dimethyl-3,4-dihydro-7H-isochromene-6,8-dione (IIa)

(IIa)

253 mg (0.85 mmol, 1 eq.) of lactol (IVa) are dissolved in 10 mL of dichloromethane at room temperature in a dried round-bottomed flask under argon. 0.45 mL (6.0 mmol, 7 eq.) of TFA and 0.95 mg (3.4 mmol, 4 eq.) of IBX are added.

After 3 hours, the suspension is filtered on a sinter funnel. The filtrate is evaporated. The residue is then purified by chromatography on silica using a cyclohexane/ethyl acetate mixture (gradually from 90/10 to 20/80). 118 mg (67%) of alcohol (IIa) are then obtained in the form of a mixture of diastereoisomers.

Analyses:

$^1$H NMR (300 MHz, CDCl$_3$) δ ppm: 1.46-1.53 (m, 6H, CH$_3$), 2.59-2.82 (m, 2H, CH$_2$), 3.76 (bs, 1H, OH), 4.36-4.43 (m, 1H, CH), 5.76 (s, 1H, CH), 7.83 (s, 1H, CH).

$^{13}$C NMR (75 MHz, CDCl$_3$) δ ppm: 20.1, 20.2, 28.9, 29.2, 35.0, 35.1, 75.39, 75.40, 83.2, 83.4, 110.9, 115.9, 116.4, 147.2, 147.6, 160.7, 195.2, 195.6, 197.5, 197.0.

13) Synthesis of 7-hydroxy-3,3,7-trimethyl-3,4-dihydro-7H-isochromene-6,8-dione (IIb)

(IIb)

Procedure similar to (IIa) but starting with (IVb). Yield=44%

Analyses:

$^1$H NMR (300 MHz, CD$_3$CN) δ ppm: 1.36 (s, 6H, H), 1.49 (s, 3H, CH$_3$), 2.66 (s, 2H, CH$_2$), 4.05 (bs, 1H, OH), 5.78 (s, 1H, CH), 7.75 (s, 1H, CH).

$^{13}$C NMR (75 MHz, CD$_3$CN) δ ppm: 25.9, 26.5, 28.9, 39.67, 81.1, 83.2, 109.6, 116.6, 147.0, 159.2, 195.2, 197.7.

Example 2

General Procedure for Preparing the Compounds (I)

For the compounds (Ia)-(Ih):

1 eq. of (IIa) or (IIb) is dissolved in 10 mL of toluene in a dried 25 mL round-bottomed flask under argon. 2 equivalents of Et$_3$N and 1.5 equivalents of dioxinone of are added.

Dioxinones bearing different groups R were used for synthesizing compounds (Ia) to (Ih) below, of general formula:

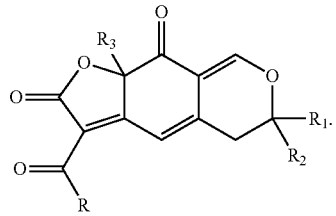

After 2 hours of reaction at 100° C. (internal temperature), the reaction is cooled to room temperature and hydrolyzed by adding 25 mL of 1N HCl.

The product is extracted from the reaction medium with 25 mL of EtOAc and the organic phase is washed with 25 mL of 1N HCl. The organic phase is then dried over $MgSO_4$, filtered and concentrated under vacuum. The product (I) is then purified by chromatography on silica gel, using a cyclohexane/ethyl acetate mixture.

The products are generally obtained in the form of a mixture of diastereoisomers that are generally not separable by column chromatography on silica gel.

For compounds (Ii)-(Io):

The experimental protocol is the same as that used for the synthesis of compounds (Ia)-(Ih), except that the dioxinone is used in its silyl enol form. The protocol for transforming the dioxinone into its silyl derivative is described below.

Dioxinones bearing different groups R were used for synthesizing compounds (Ii) to (Io).

1.3 mmol, (1 eq.) of dioxinone are dissolved in 10 mL of $CH_2Cl_2$ in a dried round-bottomed flask under argon. 3.9 mmol (3 eq.) of triethylamine and 2 mmol (1.5 eq.) of t-butyldimethylsilyl triflate are added. After 1 hour, the reaction is hydrolyzed by adding 10 mL of saturated $NaHCO_3$ solution.

The product is extracted from the reaction medium with 50 mL of EtOAc and is washed twice with 100 mL of saturated $NH_4Cl$ solution and finally twice with 50 mL of saturated NaCl solution. The organic phase is then dried over $MgSO_4$, filtered and reduced under vacuum. After purification by chromatography on silica gel, using a cyclohexane/ethyl acetate mixture (gradually from 95/5 to 90/10), the silyl dioxinone is obtained.

a) 3-benzoyl-6,9a-dimethyl-5,6-dihydro-9aH-furo[3,2-g]isochromene-2,9-dione (Ia)

($R_1$=H, $R_2$=Me, R=Ph)

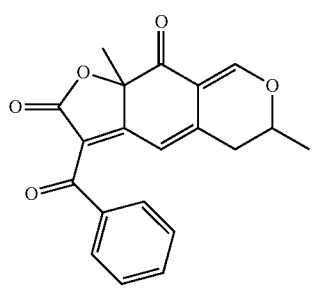 [SMILES: CC1CC2=CC3=C(C(=O)c4ccccc4)C(=O)OC3(C)C(=O)C2=CO1]

(Ia)

Analyses:
$^1$H NMR (300 MHz, $CDCl_3$) δ ppm: 1.47 (d, J=6.4 Hz, 3H, $CH_3$), 1.75 (s, 3H, $CH_3$), 2.67 (ddd, J=3.1-10.5 and 16.6 Hz, 1H, CH), 2.78 (dd, J=3.6 and 16.6 Hz, 1H, CH), 4.33 (m, 1H, CH), 6.50 (s, 1H, CH), 7.45 (t, J=7.4 Hz, 2H, $CH_{ar}$), 7.57 (t, J=7.5 Hz, 1H, $CH_{ar}$), 7.82 (s, 1H, CH), 7.83 (d, J=6.9 Hz, 2H, $CH_{ar}$).

$^{13}$C NMR (75 MHz, $CDCl_3$) δ ppm: 19.9, 27.6, 35.3, 86.8, 110.8, 111.4, 119.69, 128.4, 129.6, 133.8, 136.3, 141.9, 160.2, 168.1, 169.7, 188.9, 189.3.

b) 3-(4-methoxybenzoyl)-6,9a-dimethyl-5,6-dihydro-9aH-furo[3,2-g]isochromene-2,9-dione (Ib)

($R_1$=H, $R_2$=Me, R=p-OMePh)

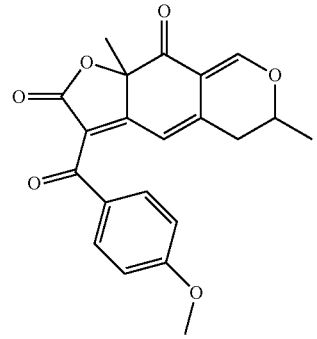 [SMILES: COc1ccc(C(=O)C2=C3C=C4CC(C)OC=C4C(=O)C3(C)OC2=O)cc1]

(Ib)

Yield=62%
Analyses:
$^1$H NMR (300 MHz, $CDCl_3$) δ ppm: 1.46 (d, J=6.4 Hz, 2.1H, $CH_3$), 1.47 (d, J=6.4 Hz, 0.9H, $CH_3$), 1.74 (s, 2.1H, $CH_3$), 1.74 (s, 0.9H, $CH_3$), 2.56 (ddd, J=1.8-11.1 and 17.0 Hz, 0.3H, CH), 2.67 (ddd, J=1.1-10.6 and 16.4 Hz, 0.7H, CH), 2.76 (dd, J=3.4 and 16.7 Hz, 1H, CH), 3.87 (s, 3H, $CH_3$), 4.35 (m, 0.7H, CH), 4.42 (m, 0.3H, CH), 6.48 (s, 1H, CH), 6.92 (d, J=8.9 Hz, 2H, $CH_{ar}$), 7.81 (s, 0.7H, CH), 7.84 (s, 0.3H, CH), 7.84 (d, J=9 Hz, 2H, $CH_{ar}$).

$^{13}$C NMR (75 MHz, $CDCl_3$) δ ppm: 20.1 (2C), 27.6, 28.0, 34.7, 35.5, 55.7 (2C), 75.5 (2C), 87.0 (2C), 110.7, 111.0, 111.7, 111.8, 113.8 (2C), 113.9 (2C), 119.72, 120.6, 129.4, 129.5, 132.3 (4C), 141.4, 141.7, 160.07, 160.12, 164.40, 164.44, 168.4, 168.6, 168.9, 169.9, 187.2, 187.3, 189.6, 190.3.

c) 3-(furan-2-carbonyl)-6,9a-dimethyl-5,6-dihydro-9aH-furo[3,2-g]isochromene-2,9-dione (Ic)

($R_1$=H, $R_2$=Me, R=2-furyl)

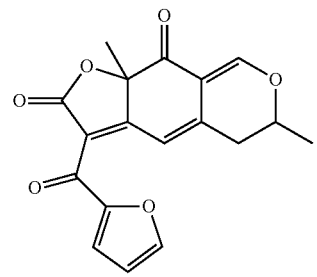

(Ic)

Yield=90%
Analyses:
$^1$H NMR (300 MHz, $CDCl_3$) δ ppm: 1.49 (d, J=6.4 Hz, 3H, $CH_3$), 1.72 (s, 1.8H, $CH_3$), 1.79 (s, 1.2H, $CH_3$), 2.60 (dd, J=11.1 and 17.1 Hz, 0.4H, CH), 2.70 (dd, J=10.7 and 16.2 Hz, 0.6H, CH), 2.82 (dd, J=2.8 and 16.4 Hz, 1H, CH), 4.33 (m, 0.6H, CH), 4.41 (m, 0.4H, CH), 6.58 (s, 1H, CH), 6.75 (s, 1H, $CH_{ar}$), 7.60 (s, 1H, $CH_{ar}$), 7.68 (s, 1H, $CH_{ar}$), 7.82 (s, 0.6H, CH), 7.85 (s, 0.4H, CH).

$^{13}$C NMR (75 MHz, $CDCl_3$) δ ppm: 20.0, 20.1, 27.7, 28.1, 34.8, 35.5, 75.57, 75.63, 86.98, 87.00, 111.1, 111.5, 111.6, 111.8, 112.9 (2C), 118.0, 119.2, 122.4, 122.5, 142.4, 142.9, 148.1, 148.2, 151.57, 151.62, 160.4 (2C), 167.8, 168.0, 171.1, 172.1, 174.56, 174.63, 189.5, 190.2.

d) 3-(2-naphthoyl)-6,9a-dimethyl-5,6-dihydro-9aH-furo[3,2-g]isochromene-2,9-dione (Id)

($R_1$=H, $R_2$=Me, R=2-naphthyl)

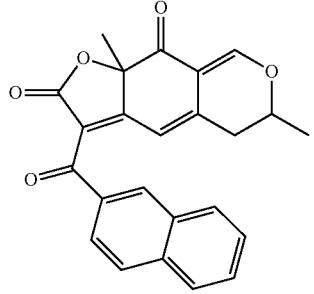 [SMILES: CC1CC2=CC3=C(C(=O)c4ccc5ccccc5c4)C(=O)OC3(C)C(=O)C2=CO1]

(Id)

Yield=62%.
Analyses:
$^1$H NMR (300 MHz, CDCl$_3$) δ ppm: 1.45 (d, J=6.2 Hz, 1.5H, CH$_3$), 1.46 (d, J=6.2 Hz, 1.5H, CH$_3$), 1.79 (s, 1.5H, CH$_3$), 1.85 (s, 1.5H, CH$_3$), 2.55 (dd, J=10.7 and 16.6 Hz, 0.5H, CH), 2.66 (dd, J=10.9 and 16.8 Hz, 0.5H, CH), 2.76 (d, J=16.6 Hz, 0.5H, CH), 2.77 (d, J=16.8 Hz, 0.5H, CH), 4.32 (m, 0.5H, CH), 4.42 (m, 0.5H, CH), 6.51 (s, 0.5H, CH), 6.53 (s, 0.5H, CH), 7.51-7.63 (m, 2H, CH$_{ar}$), 7.83-7.95 (m, 5H, 4CH$_{ar}$+1CH), 7.84 (s, 1H, CH$_{ar}$).
$^{13}$C NMR (75 MHz, CDCl$_3$) δ ppm: 20.0, 20.1, 27.7, 28.1, 34.7, 35.4, 75.5 (2C), 87.1 (2C), 110.7, 111.0, 111.7, 111.8, 119.3, 120.2, 124.68, 124.72, 127.0 (2C), 127.9 (2C), 128.5 (2C), 129.0 (2C), 130.0 (2C), 132.3 (2C), 132.4 (20) 133.85, 133.94, 136.1 (2C), 142.0, 142.3, 160.3 (2C), 168.3, 168.4, 169.7, 170.6, 188.86, 188.9, 189.6, 190.2.

e) 3-(4-(2-(2-methoxyethoxy)ethoxy)benzoyl)-6,9a-dimethyl-5,6-dihydro-9aH-furo[3,2-g]isochromene-2,9-dione (Ie)

($R_1$=H, $R_2$=Me, R=4-(2-(2-methoxyethoxy)ethoxy)phenyl)

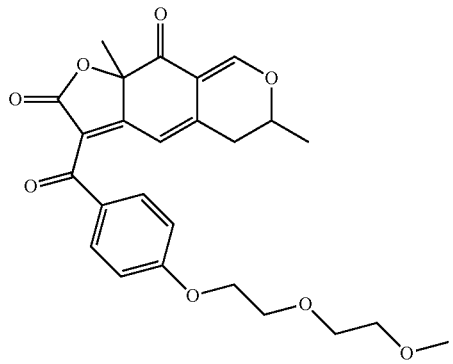 [SMILES: COCCOCCOc1ccc(C(=O)C2=C3C=C4CC(C)OC=C4C(=O)C3(C)OC2=O)cc1]

(Ie)

Yield=15%
Analyses:
$^{13}$H NMR (300 MHz, CDCl$_3$) δ ppm: 1.47 (d, J=6.4 Hz, 3H, CH$_3$), 1.74 (s, 3H, CH$_3$), 2.67 (dd, J=10.6 and 16.4 Hz, 1H, CH), 2.78 (dd, J=3.8 and 16.5 Hz, 1H, CH), 3.39 (s, 3H, CH$_3$), 3.57 (dd, J=2.8 Hz and 4.9 Hz 0.2H, CH$_2$), 3.71 (t, J=2.9 Hz and 4.9 Hz, 2H, CH$_2$), 3.87 (t, J=4.5 Hz, 2H, CH$_2$), 4.21 (t, J=4.5 Hz, 2H, CH$_2$), 4.31 (m, 1H, CH), 6.46 (s, 1H, CH), 6.94 (d, J=8.9 Hz, 2H, CH$_{ar}$), 7.82 (s, 1H, CH), 7.83 (d, J=8.9 Hz, 2H, CH$_{ar}$).
$^{13}$C NMR (75 MHz, CDCl$_3$) δ ppm: 19.0, 26.5, 34.3, 58.1, 66.6, 68.5, 69.8, 70.9, 74.3, 85.8, 109.9, 110.5, 113.3, 119.5, 128.4, 131.2, 140.2, 158.9, 162.5, 167.4, 167.7, 186.1, 188.5.

f) 3-(2-methoxybenzoyl)-6,9a-dimethyl-5,6-dihydro-9aH-furo[3,2-g]isochromene-2,9-dione (If)

($R_1$=H, $R_2$=Me, R=2-methoxyphenyl)

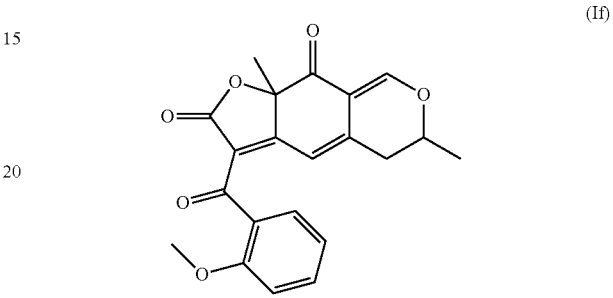

(If)

Yield=27%
Analyses:
$^1$H NMR (300 MHz, CDCl$_3$) δ ppm: 1.48 (d, J=6.2 Hz, 3H, CH$_3$), 1.70 (s, 3H, CH$_3$), 2.69 (dd, J=10.9 and 16.2 Hz, 1H, CH), 2.83 (dd, J=3.2 and 16.4 Hz, 1H, CH), 3.76 (s, 3H, CH$_3$), 4.35 (m, 1H, CH), 6.75 (s, 1H, CH), 6.92 (d, J=8.3 Hz, 1H, CH$_{ar}$), 7.02 (t, J=7.4 Hz, 2H, CH$_{ar}$), 7.47 (t, J=7.9 Hz, 2H, CH$_{ar}$), 7.54 (t, J=7.6 Hz, 1H, CH$_{ar}$), 7.80 (s, 1H, CH).
$^{13}$C NMR (75 MHz, CDCl$_3$) δ ppm: 20.3, 27.7, 35.7, 56.0, 75.7, 86.5, 111.7, 111.98, 112.03, 121.2, 122.0, 128.2, 130.6, 134.6, 141.6, 159.3, 159.9, 167.3, 168.3, 189.0, 190.2.

g) 3-(2-hydroxybenzoyl)-6,9a-dimethyl-5,6-dihydro-9aH-furo[3,2-g]isochromene-2,9-dione (Ig)

($R_1$=H, $R_2$=Me, R=2-hydroxyphenyl)

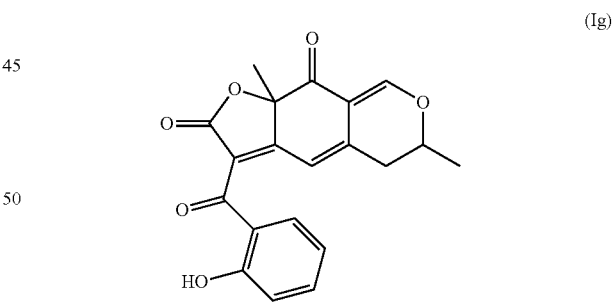

(Ig)

36 mg (0.1 mmol, 1 eq.) of derivative (If) and 100 mg (0.8 mmol, 8 eq.) of AlCl$_3$ are dissolved in 20 mL of dichloromethane in a dried round-bottomed flask under argon. After 1 hour 30 minutes, the reaction is hydrolyzed with 50 mL of 1N HCl at 0° C.

After separating out the organic phase, the aqueous phase is re-extracted with 2×100 mL of EtOAc. The organic phase is then dried over MgSO$_4$, filtered and evaporated under vacuum. 2.71 g (100%) of pure product are then obtained after precipitation from a minimum amount of dichloromethane. 30 mg (85%) of pro-fluorophore (Ig) are obtained.

Analyses:

$^1$H NMR (300 MHz, CDCl$_3$) δ ppm: 1.49 (d, J=6.4 Hz, 3H, CH$_3$), 1.77 (s, 3H, CH$_3$), 2.69 (dd, J=10.6 and 16.4 Hz, 1H, CH), 2.79 (dd, J=3.6 and 16.8 Hz, 1H, CH), 4.35 (m, 1H, CH), 6.35 (s, 1H, CH), 6.91 (t, J=7.9 Hz, 1H, CH$_{ar}$), 7.02 (d, J=8.1 Hz, 1H, CH$_{ar}$), 7.53 (t, J=7.2 Hz, 1H, CH$_{ar}$), 7.61 (d, J=8.1 Hz, 1H, CH$_{ar}$), 7.85 (s, 1H, CH), 11.82 (s, 1H, OH).

$^{13}$C NMR (75 MHz, CDCl$_3$) δ ppm: 20.2, 27.7, 35.5, 75.7, 87.3, 110.3, 111.5, 118.5, 119.4, 119.5, 119.9, 132.8, 137.9, 142.1, 160.7, 163.3, 168.0, 168.3, 189.3, 193.2.

h) 3-(4-methoxybenzoyl)-6,6,9a-trimethyl-5,6-dihydro-9aH-furo[3,2-g]isochromene-2,9-dione (Ih)

(R$_1$=Me R$_2$=Me, R=4-methoxyphenyl)

(Ih)

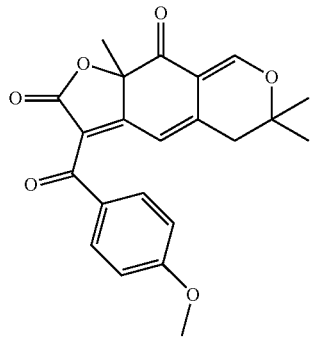 [SMILES: COc1ccc(C(=O)C2=C3C=C4CC(C)(C)OC=C4C(=O)C3(C)OC2=O)cc1]

Yield=86%

Analyses:

$^1$H NMR (300 MHz, CDCl$_3$) δ ppm: 1.36 (s, 3H, CH$_3$), 1.42 (s, 3H, CH$_3$), 1.76 (s, 3H, CH$_3$), 2.57 (q, J=16.58-26.37 Hz, 2H, CH$_2$), 3.86 (s, 3H, CH$_3$), 6.47 (s, 1H, CH), 6.91 (d, J=9.05 Hz, 2H, CH$_{ar}$), 7.74 (s, 1H, CH), 7.82 (d, J=8.85 Hz, 2H, CH$_{ar}$).

$^{13}$C NMR (75 MHz, CDCl$_3$) δ ppm: 26.3, 26.4, 27.9, 39.8, 55.7, 81.2, 87.0, 110.6, 111.4, 113.8, 119.9, 129.4, 132.3, 141.4, 158.8, 164.4, 168.5, 169.3, 187.2, 189.8.

i) (Z)-3-(3-hydroxy-3-(4-methoxyphenyl)acryloyl)-6,9a-dimethyl-5,6-dihydro-9aH-furo[3,2-g]isochromene-2,9-dione (Ii)

(R$_1$=H, R$_2$=Me, R=2-(4-methoxyphenyl)-2-hydroxyethenyl)

(Ii)

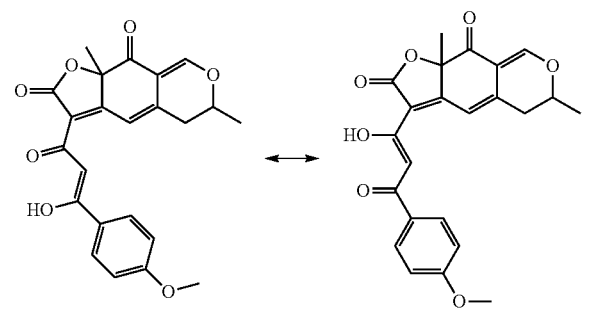

Yield=12%

Analyses:

$^1$H NMR (300 MHz, CDCl$_3$) δ ppm: 1.49 (d, J=6.4 Hz, 1.8H, CH$_3$), 1.50 (d, J=6.4 Hz, 1.2H, CH$_3$), 1.69 (s, 1.2H, CH$_3$), 1.76 (s, 1.8H, CH$_3$), 2.65 (ddd, J=1.7-10.73 and 17.0 Hz, 0.6H, CH), 2.73 (ddd, J=1.5-11.1 and 16.8 Hz, 0.4H, CH), 2.87 (dd, J=2.8 and 17.1 Hz, 1H, CH), 3.88 (s, 3H, CH$_3$), 4.35 (m, 0.4H, CH), 4.45 (m, 0.6H, CH), 6.95 (d, J=9.0 Hz, 2H, CH$_{ar}$), 7.07 (s, 0.4H, CH), 7.09 (s, 0.6H, CH), 7.44 (s, 1H, CH), 7.81 (s, 0.4H, CH), 7.84 (s, 0.6H, CH), 8.00 (d, J=8.9 Hz, 2H, CH$_{ar}$).

$^{13}$C NMR (75 MHz, CDCl$_3$) δ ppm: 20.2, 20.4, 27.9, 28.3, 35.1, 35.9, 55.9 (2C), 75.79, 75.84, 86.7 (2C), 97.1, 97.14, 111.9, 112.0, 113.0, 113.4, 114.3 (4C), 114.6, 115.4, 128.8 (2C), 130.41 (2C), 130.44 (2C), 141.1, 141.4, 160.1, 160.2, 164.09, 164.13, 166.9, 167.9, 168.6, 168.7, 173.0 (2C), 189.9, 190.5, 190.57, 190.64.

j) (Z)-3-(3-hydroxy-3-(4-methoxyphenyl)acryloyl)-6,6,9a-trimethyl-5,6-dihydro-9aH-furo[3,2-g]isochromene-2,9-dione (Ij)

(R$_1$=Me, R$_2$=Me, R=2-(4-methoxyphenyl)-2-hydroxyethenyl)

(Ij)

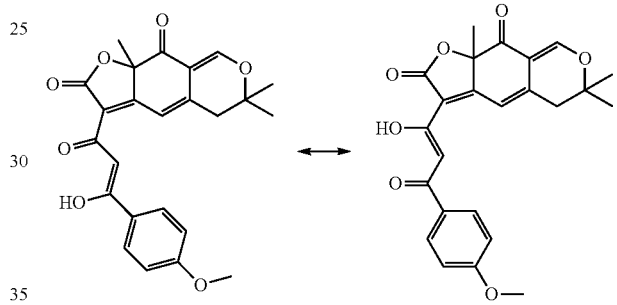

Yield=15%

Analyses:

$^1$H NMR (300 MHz, CDCl$_3$) δ ppm: 1.39 (s, 3H, CH$_3$), 1.42 (s, 3H, CH$_3$), 1.72 (s, 3H, CH$_3$), 2.73 (d, J=6.78 Hz, 2H, CH$_2$), 3.88 (s, 3H, CH$_3$), 6.94 (d, J=9.03 Hz, 2H, CH$_{ar}$), 7.10 (s, 1H, CH), 7.45 (s, 1H, CH), 7.75 (s, 1H, CH), 7.99 (d, J=8.85 Hz, 2H, CH$_{ar}$).

$^{13}$C NMR (75 MHz, CDCl$_3$) δ ppm: 26.2, 26.6, 28.0, 40.1, 55.7, 81.3, 86.5, 96.9, 110.7, 113.6, 114.1, 114.7, 128.6, 130.2, 140.9, 158.8, 163.9, 167.3, 168.5, 172.6, 189.9, 190.4.

k) (Z)-3-(3-hydroxy-3-phenylacryloyl)-6,6,9a-trimethyl-5,6-dihydro-9aH-furo[3,2-g]isochromene-2,9-dione (Ik)

(R$_1$=Me, R$_2$=Me, R=2-phenyl-2-hydroxyethenyl)

(Ik)

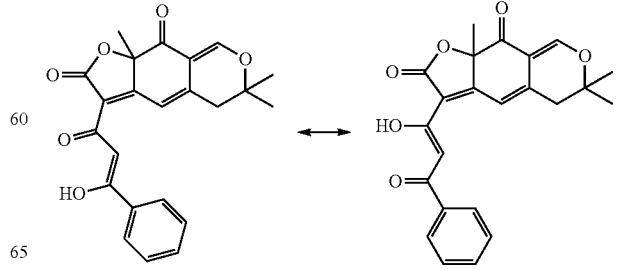

Yield=39%

Analyses:

$^1$H NMR (300 MHz, CDCl$_3$) δ ppm: 1.40 (s, 3H, CH$_3$), 1.46 (s, 3H, CH$_3$), 1.73 (s, 3H, CH$_3$), 2.71 (d, J=16.6 Hz, 1H, CH), 2.78 (d, J=16.6 Hz, 1H, CH), 7.11 (s, 1H, CH), 7.46 (t, J=7.2 Hz, 2H, CH$_{ar}$), 7.50 (s, 1H, CH), 7.55 (t, J=7.2 Hz, 1H, CH$_{ar}$), 7.76 (s, 1H, CH), 8.00 (d, J=7.4 Hz, 2H, CH$_{ar}$).

$^{13}$C NMR (75 MHz, CDCl$_3$) δ ppm: 26.2, 26.5, 28.0, 40.1, 81.4, 86.5, 97.3, 110.7, 113.5, 114.6, 127.9, 128.8, 133.2, 135.2, 141.4, 159.0, 168.1, 168.3, 174.4, 189.8, 190.5.

l) 3-(3-(4-methoxyphenyl)-2-methyl-3-oxopropanoyl)-6,6,9a-trimethyl-5,6-dihydro-9aH-furo[3,2-g]isochromene-2,9-dione (Il)

(R$_1$=Me, R$_2$=Me, R=2-[1-(4-methoxyphenyl)-1-oxo-2-methyl)propyl)

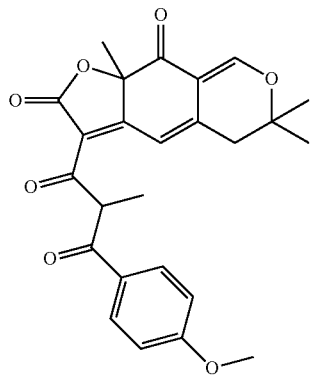

(Il)

Yield=25%

Analyses:

$^1$H NMR (300 MHz, CDCl$_3$) δ ppm: 1.40 (m, 9H, 3×CH$_3$), 1.69 (s, 3H, CH$_3$), 2.70 (d, J=3.21 Hz, 2H, CH$_2$), 3.86 (s, 3H, CH$_3$), 5.47 (q, J=6.96 and 13.71 Hz, 1H, CH), 6.92 (d, J=8.85 Hz, 2H, CH$_{ar}$), 7.09 (s, 1H, CH), 7.76 (s, 1H, CH), 7.93 (d, J=8.85 Hz, 2H, CH$_{ar}$).

$^{13}$C NMR (75 MHz, CDCl$_3$) δ ppm: 13.5, 26.3, 26.6, 28.4, 40.0, 52.3, 55.6, 81.6, 86.6, 110.8, 112.8, 114.1, 115.9, 128.7, 131.2, 144.4, 159.7, 163.8, 169.1, 172.9, 189.5, 193.7, 197.3.

m) 6,6,9a-trimethyl-3-(2-methyl-3-oxo-3-phenylpropanoyl)-5,6-dihydro-9aH-furo[3,2-g]isochromene-2,9-dione (Im)

(R$_1$=Me, R$_2$=Me, R=2-(1-phenyl-1-oxo-2-methyl)propyl)

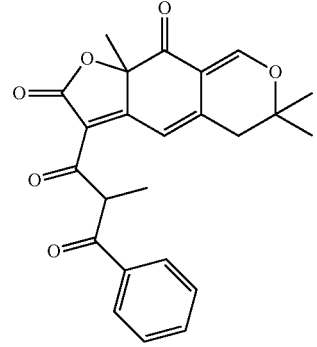 [SMILES: CC1(C)CC2=CC3=C(C(=O)/C=C(\O)c4ccccc4)C(=O)OC3(C)C(=O)C2=CO1]

(Im)

Yield=29%

Analyses:

$^1$H NMR (300 MHz, CDCl$_3$) δ ppm: 1.40-1.45 (m, 9H, CH$_3$), 1.69 (d, J=3.21 Hz, 3H, CH$_3$), 2.72 (s, 2H, CH$_2$), 5.45-5.61 (m, 1H, CH), 7.09 (s, 1H, CH), 7.45-7.57 (m, 3H, CH$_{ar}$), 7.76 (s, 1H, CH$_{ar}$), 7.95-8.00 (m, 2H, CH$_{ar}$).

$^{13}$C NMR (75 MHz, CDCl$_3$) δ ppm: 13.0, 13.3, 26.3, 26.4, 26.5, 28.3, 28.4, 40.0, 52.6, 52.7, 81.58, 81.61, 86.7, 86.8, 110.6, 110.7, 112.8, 113.0, 115.6, 115.9, 128.9, 133.4, 135.7, 135.8, 144.1, 144.6, 159.6, 159.8, 169.15, 169.21, 172.7, 173.1, 189.5, 189.7, 193.5, 193.6, 198.7, 199.2.

n) 3-[3-(6-chloro-pyridin-3-yl)-1-hydroxy-3-oxopropenyl]-6,6,9a-trimethyl-5,6-dihydro-9aH-furo[3,2-g]isochromene-2,9-dione (In)

(R1=Me, R2=Me, R=2-(6-chloropyridin-3-yl)-2-hydroxy-ethenyl)

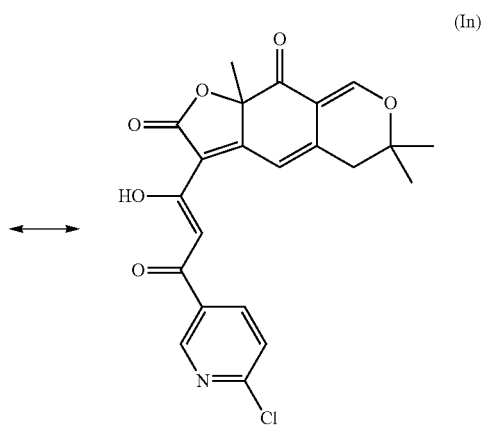

(In)

Yield=15%

Analyses:

$^{13}$H NMR (300 MHz, CDCl$_3$) δ ppm: 8.97 (d, J=2.2 Hz, 1H), 8.19 (dd, J=2.2 and 8.3 Hz, 1H), 7.78 (s, 1H), 7.44 (m, 2H), 7.08 (s, 1H), 2.76 (m, 2H), 1.73 (s, 3H), 1.47 (s, 3H), 1.40 (s, 3H).

$^{13}$C NMR (75 MHz, CDCl$_3$) δ ppm: 189.6, 186.8, 175.7, 169.3, 168.3, 159.5, 155.5, 149.5, 142.5, 137.6, 130.3, 124.5, 113.9, 113.2, 110.6, 97.2, 86.7, 81.5, 40.1, 28.2, 26.5, 26.3.

HRMS (high resolution mass spectroscopy): mass calculated for C$_{22}$H$_{17}$NO$_6$Cl: 426.0744, measured mass: 426.0754.

o) 3-(1-hydroxy-3-naphtalen-2-yl-3-oxopropenyl)-6,6,9a-trimethyl-5,6-dihydro-9aH-furo[3,2-g]isochromene-2,9-dione (Io)

(R1=Me, R2=Me, R=2-[(2-naphthyl)-2-hydroxyethenyl)

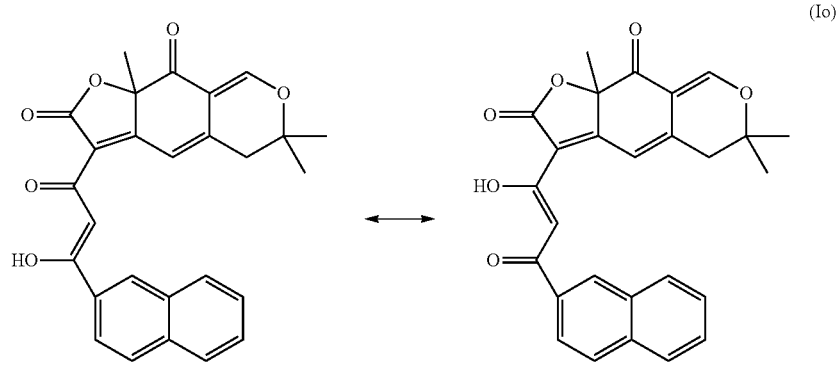

(Io)

Yield=26%

Analyses:

$^1$H NMR (300 MHz, CDCl$_3$) δ ppm: 8.55 (s, 1H), 8.07-7.98 (m, 2H), 7.92-7.85 (m, 3H), 7.77 (s, 1H), 7.65 (s, 1H), 7.62-7.55 (m, 2H), 7.13 (s, 1H), 2.75 (m, 2H), 1.75 (s, 3H), 1.47 (s, 3H), 1.40 (s, 3H).

$^{13}$C NMR (75 MHz, CDCl$_3$) δ ppm: 190.3, 189.9, 174.4, 168.5, 168.1, 159.0, 141.4, 135.7, 133.1, 132.8, 129.9, 129.4, 128.7, 128.6, 127.9, 126.9, 123.6, 114.6, 113.5, 110.7, 97.5, 86.6, 81.4, 40.1, 28.1, 26.5, 26.3.

HRMS (high resolution mass spectroscopy): mass calculated for C$_{27}$H$_{23}$O$_6$: 443.1495, measured mass: 443.1500.

Example 3

Absorption and Emission of Compounds (Ia) to (Io) and of the Adducts Thereof

Apparatus:
Acetonitrile: VWR HPLC quality
Micropipette: 5 µl, 10 µl, 200 µl, 1000 µl,
Eppendorf: Safe lock tube PCR
UV cuvette: Varian-Quartz 10 mm thick
Fluorescence cuvette: Hellma-Quartz 10 mm thick
Vortex: Bender & Hobein-Genie 2
Centrifuge: Baky Bug
Absorbance spectrophotometer: Varian-Cary 50 scan
Fluorescence spectrophotometer: Varian-Cary Eclipse
Thermostated bath: Varian-Cary single cell peltier accessory Stock Solution:
Approximately exactly 1 to 2 mg of compound Ia-Io are weighed out in a 1.5 mL Eppendorf tube. The stock solutions are then prepared by adding exactly 1 mL of acetonitrile and the Eppendorf tubes are then stored protected from light.

Absorbance and Fluorescence of the Adducts with Butylamine:

Absorbance:

30 µl of stock solution are placed in a 1.5 mL Eppendorf tube. At room temperature, 10 µl (or 30 µl in the case of Ik) of a 0.15 M solution of butylamine/acetonitrile are added and the medium is stirred by vortex and then centrifuged. After diluting to 1 mL by adding 960 µl of acetonitrile (or 940 µl in the case of Ik), the clear solution is transferred into a UV cuvette and then made up to 2 mL with acetonitrile. The analysis is then performed after producing a "blank" spectrum with a pure acetonitrile solution.

Fluorescence:

Two protocols were implemented for the fluorescence tests.

For compounds Ii-Ik: 125 µL of the preceding solution (absorbance solution) are diluted to 1.25 mL by adding 1125 µl of acetonitrile to a fluorescence cuvette. The analysis is then performed on the fluorescence spectrophotometer by excitation at the respective maximum-absorption wavelengths.

For compounds Ia-Ih and Il-Io: 1250 µl of the preceding solution (absorbance) are placed in a fluorescence cuvette. The analysis is then performed on the fluorescence spectrophotometer by excitation at the respective maximum-absorption wavelengths.

UV and fluorescence table for the biconjugated derivatives of Ia-Io with butylamine.

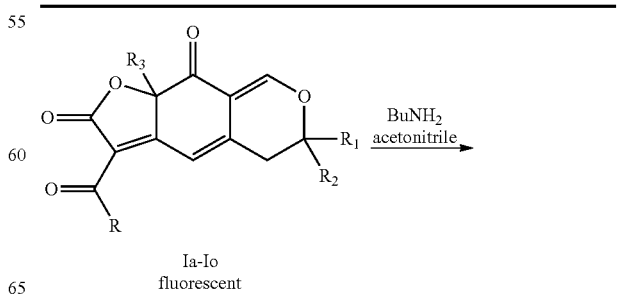

Ia-Io
fluorescent

-continued

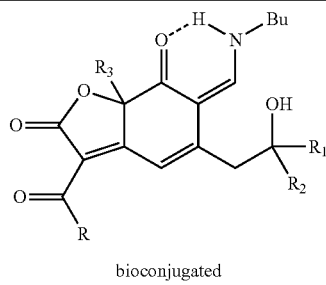

bioconjugated

| Initial compound | λ UV (nm) | λ fluo (λ excitation) (nm) | Δ Stokes | Intensity normalized to 50 µM |
|---|---|---|---|---|
| Ia | 351/472 | 585 (exc 472) | 113 | 98 |
| Ib | 351/452 | 586 (exc 452) | 134 | 205 |
| Ic | 352/465 | 593 (exc 465) | 128 | 193 |
| Id | 351/464 | 570 (exc 464) | 106 | 173 |
| Ie | 349/453 | 590 (exc 453) | 137 | 120 |
| If | 351/469 | 589 (exc 469) | 120 | 147 |
| Ig | 350/463 | 597 (exc 463) | 134 | 32 |
| Ih | 354/460 | 590 (exc 460) | 130 | 155 |
| Ii | 366/497 | 596 (exc 497) | 99 | 3020 |
| Ij | 366/505 | 603 (exc 505) | 98 | 3988 |
| Ik | 365/512 | 606 (exc 512) | 94 | 4157 |
| Il | 350/498 | 588 (exc 498) | 90 | 264 |
| Im | 351/489 | 591 (exc 489) | 102 | 202 |
| In | 363/525 | 612 (exc 525) | 87 | 2764 |
| Io | 364/520 | 609 (exc 520) | 89 | 4320 |
| epicocconone | 388/515 | 610 (exc 515) | 95 | 3950 |

Bioconjugated molecule (BuNH$_2$) in CH$_3$CN

Example 4

Photobleaching of Compounds (Ii), (Ij), (Ik), (In) and (Io)

Experimental Protocol:

The compounds were dissolved at 10 mg/mL in DMSO. The stock solutions obtained were diluted to 1 mg/mL in water and divided into 100 µL aliquots for storage. All the products and aliquots were stored at −80° C.

Standard proteins (SDS labeling kit-low molecular weight sold by GE, 17-0446-01) were diluted in an LDS buffer (250 µL Invitrogen 4×LDS buffer, 100 µL of 1 M DDT, 650 µL of water) to create serial dilutions ranging from 128 ng/STI band to 125 pg/STI band.

5 µL of each protein solution were loaded onto NuPAGE® Novex® 12% bis-tris gels (1.0 mm thick, 12 wells, Invitrogen NP0342BOX). The gels were subjected to a current of 150 V for approximately 65 minutes using MES buffer (50 mM MES, 50 mM tris, 1 mM EDTA, 0.1% SDS, pH 7.3) so that the buffer front arrives just up to the gel. After eluting the dye, the gels were fixed for 1 to 17 hours (100 mL of fixing solution with 15% EtOH (v/v) and 1% citric acid) in individual lanes. The fixing solution used was replaced with fresh solution one hour after staining. The gels were stained for 1 hour in 50 mL of sodium borate buffer at 100 mM (pH 10.9) containing either 250 mL of LavaPurple gel dye (Fluorotechnics; LP-011005) or one of the test compounds (50 µL for a 1 mg/mL solution). The gels were treated with 100 mL of 15% ethanol and then washed with 100 mL of fixing solution for 30 minutes.

Imaging was performed using a Typhoon Trio imager (excitation: 532 nm, emission filter: 610BP30, 540 PMT, resolution: 100 µm) using a normal sensitivity. The recorded image corresponds to the scan at time zero. The gels were then placed in a UV transilluminator for 60, 146, 240, 330, 630 and 990 seconds (total exposure time), a Typhoon scanner image being recorded between each exposure. The volumes of the bands were analyzed using the Image-Quant TL software, and all the band volumes were normalized with phosphorylase B. The photobleaching was analyzed by graphically representing the band volumes as a function of the exposure time (GraphPad Prism v4 software) and by fitting the curve to a first-order exponential decay to determine a pseudofirst-order rate constant.

FIG. 1 represents the decrease of the normalized residual signal of compounds (Ii), (Ij), (Ik), (In) and (Io) according to the invention and of epicocconone.

From this FIGURE, the half-life times of the compounds may be deduced:

| Compound | Curve number in FIG. 1 | Half-life time (in minutes) |
|---|---|---|
| Io | 1 | 44.7 |
| In | 2 | 33.1 |
| Ik | 3 | 22.4 |
| Ii | 4 | 18.3 |
| epicocconone | 5 | 11.3 |
| Ij | 6 | 6.6 |

The invention claimed is:
1. A compound of formula (I')

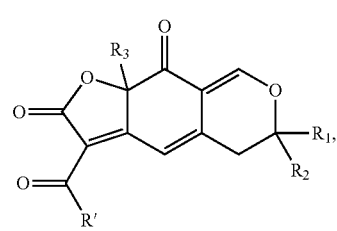

(I')

tautomers thereof, stereoisomers thereof and mixtures thereof, in which

R1, R2 and R3 are each independently selected from a hydrogen, and
a C1 to C20 alkyl chain,
R' represents -A-C',
A denoting a chemical bond or a linear or branched divalent radical, containing 1 to 20 carbon atoms, which may optionally comprise one or more heteroatoms selected from O, N, S and P, and which may comprise one or more unsaturations, and which may be optionally substituted with one or more identical or different substituents selected from a halogen, a hydroxyl group and an oxo group, and C' being a monocyclic or polycyclic group, which may optionally comprise one or more heteroatoms selected from O, N, S and P, optionally containing one or more unsaturations and being optionally substituted with one or more identical or different substituents chosen from a halogen, a linear or branched alkyl chain, a linear or branched alkenyl chain, a hydroxyl, oxo, amino, alkylamino, imino, alkylimino, enamine, acyl, alkyloxy, alkenyloxy, alkynyloxy, aryl or heteroaryl group and a group of poly(alkyloxy) type of formula —O—([C1 to C4 alkyl chain]-O)$_n$—(C1 to C4 alkyl chain), n being 1 to 10.

2. The compound according to claim 1 wherein $R_1$ is methyl, $R_2$ is methyl, and R is 2-[(2-naphthyl)-2-hydroxy-ethenyl].

* * * * *